(12) United States Patent
Suga et al.

(10) Patent No.: US 12,378,518 B2
(45) Date of Patent: Aug. 5, 2025

(54) DIFFERENTIATION INDUCTION FROM HUMAN PLURIPOTENT STEM CELLS INTO HYPOTHALAMIC NEURONS

(71) Applicant: National University Corporation Nagoya University, Nagoya (JP)

(72) Inventors: Hidetaka Suga, Nagoya (JP); Koichiro Ogawa, Nagoya (JP); Takatoshi Kasai, Nagoya (JP); Hiroshi Arima, Nagoya (JP)

(73) Assignee: National University Corporation Nagoya University, Nagoya (JP)

( * ) Notice: Subject to any disclaimer, the term of this patent is extended or adjusted under 35 U.S.C. 154(b) by 322 days.

(21) Appl. No.: 16/068,929

(22) PCT Filed: Jan. 18, 2017

(86) PCT No.: PCT/JP2017/001544
§ 371 (c)(1),
(2) Date: Jul. 10, 2018

(87) PCT Pub. No.: WO2017/126551
PCT Pub. Date: Jul. 27, 2017

(65) Prior Publication Data
US 2019/0010452 A1    Jan. 10, 2019

(30) Foreign Application Priority Data

Jan. 22, 2016 (JP) ................... 2016-010940

(51) Int. Cl.
*C12N 5/0793* (2010.01)
*C12N 1/00* (2006.01)
*C12N 5/071* (2010.01)

(52) U.S. Cl.
CPC ............ *C12N 5/0619* (2013.01); *C12N 1/00* (2013.01); *C12N 5/0616* (2013.01); *C12N 2500/02* (2013.01); *C12N 2501/13* (2013.01); *C12N 2501/155* (2013.01); *C12N 2501/41* (2013.01); *C12N 2501/727* (2013.01); *C12N 2501/999* (2013.01); *C12N 2502/076* (2013.01); *C12N 2502/081* (2013.01); *C12N 2506/02* (2013.01); *C12N 2506/03* (2013.01); *C12N 2506/45* (2013.01); *C12N 2527/00* (2013.01); *C12N 2533/32* (2013.01); *C12N 2533/52* (2013.01)

(58) Field of Classification Search
CPC ...... C12N 5/0619; C12N 1/00; C12N 5/0616; C12N 2500/02; C12N 2501/13; C12N 2501/155; C12N 2501/41; C12N 2501/727; C12N 2501/999; C12N 2502/076; C12N 2502/081; C12N 2506/02; C12N 2506/03; C12N 2506/45; C12N 2527/00; C12N 2533/32; C12N 2533/52

USPC ......................................................... 435/368
See application file for complete search history.

(56) References Cited

U.S. PATENT DOCUMENTS

| | | | | |
|---|---|---|---|---|
| 10,760,047 | B2 * | 9/2020 | Sasai | C12N 5/0618 |
| 10,808,224 | B2 * | 10/2020 | Sasai | C12N 5/0618 |
| 2006/0211109 | A1 * | 9/2006 | Totey | A61P 25/08 |
| | | | | 435/368 |
| 2014/0308743 | A1 * | 10/2014 | Sasai | C12N 5/0616 |
| | | | | 435/373 |
| 2015/0361393 | A1 | 12/2015 | Nicholas et al. | |
| 2016/0289635 | A1 | 10/2016 | Sasai et al. | |
| 2020/0370010 | A1 * | 11/2020 | Sasai | C12N 5/0606 |
| 2021/0040444 | A1 * | 2/2021 | Sasai | C12N 5/0618 |

FOREIGN PATENT DOCUMENTS

| | | |
|---|---|---|
| AU | 2015293077 A | 2/2017 |
| WO | 2013/065763 A1 | 5/2013 |
| WO | 2014/153230 A1 | 9/2014 |
| WO | 2015/076388 A1 | 5/2015 |
| WO | 2016/013669 A1 | 1/2016 |

OTHER PUBLICATIONS

Merkle et al. "Generation of neuropeptidergic hypothalamic neurons from human pluripotent stem cells." Development 142.4 (2015): 633-643 (Year: 2015).*
Wataya et al. "Minimization of exogenous signals in ES cell culture induces rostral hypothalamic differentiation." Proceedings of the National Academy of Sciences 105.33 (2008): 11796-11801 (Year: 2008).*
T. Wataya et al., "Minimization of exogenous signals in ES cell culture induces rostral hypothalamic differentiation," Proc Natl Acad Sci USA , Aug. 19, 2008, vol. 105, No. 33, pp. 11796-11801. (discussed in the spec and cited in the ISR).
F. T. Merkle et al., "Generation of neuropeptidergic hypothalamic neurons from human pluripotent stem cells," Development, 2015, vol. 142, No. 4, pp. 633-643. (discussed in the spec and cited in the ISR).

(Continued)

*Primary Examiner* — Fereydoun G Sajjadi
*Assistant Examiner* — Alexander W Nicol
(74) *Attorney, Agent, or Firm* — Troutman Pepper Locke LLP

(57) ABSTRACT

There is provided a method for efficient differentiation induction from human pluripotent stem cells into hypothalamic neurons. Also, provided is a method for constructing, from human pluripotent stem cells, a cellular structure in which hypothalamic tissue and pituitary tissue are integrated. A cellular structure including hypothalamic tissue is obtained by a method including the steps of: culturing an aggregate of human pluripotent stem cells in suspension in a medium containing a low concentration of a bone morphogenetic protein signal transduction pathway activating substance and a low concentration of a substance acting on the Shh signaling pathway; and further culturing the cell aggregate obtained in the step in suspension in a medium containing a low concentration of a substance acting on the Shh signaling pathway.

7 Claims, 25 Drawing Sheets

(56) References Cited

OTHER PUBLICATIONS

C. Ozone et al., "Functional anterior pituitary generated in self-organizing culture of human embryonic stem cells," Nat. Commun., 7 :10351, Jan. 14, 2016, pp. 1-10. (discussed in the spec and cited in the ISR).

F. Otsuka, "Multiple Endocrine Regulation by Bone Morphogenetic Protein System," Endocrine J., 2010 vol. 57 No. 1, pp. 3-14. (cited in the ISR).

H. Suga et al. "Tanosei Kansaibo kara Shishokabu Kasuitai eno Bunka",Gendaiigaku, 2013 vol. 61 No. 2, pp. 191-199. (cited in the ISR).

Y. Wang et al. "Direct and indirect requirements of Shh/Gli signaling in early pituitary development" Dev. Biol., 2010, vol. 348, No. 2, pp. 199-209.

Ochiai H. et al. "BMP4 and FGF strongly induce differentiation of mouse ES cells into oral ectoderm," Stem Cell Research, 2015, vol. 15, pp. 290-298.

International Search Report mailed Apr. 18, 2017, issued for PCT/JP2017/001544.

Chikafumi Ozone et al., "Functional Anterior Pituitary Generated in Self-Organizing Culture of Human Embryonic Stem Cells", Nature Communications, vol. 7, No. 1, Jan. 14, 2016, pp. 1-10. (cited in the Jul. 29, 2019 Search Report issued for the European patent application No. 17 74 1428.1).

F. T. Merkle et al., "Generation of neuropeptidergic hypothalamic neurons from human pluripotent stem cells", Development, vol. 142, No. 4, 2015, pp. 633-643 and additional pages. (cited in the Jul. 29, 2019 Search Report Issued for the European patent application No. 17 74 1428.1).

Ochiai Hiroshi et al., "BMP4 and FGF Strongly Induce Differentiation of Mouse ES Cells into Oral Dctoderm", Stem Cell Research, vol. 15, No. 2, 2015, pp. 290-298. (cited in the Jul. 29, 2019 Search Report issued for the European patent application No. 17 74 1428.1).

Peter Kirwan et al., "Generation and Characterization of Functional Human Hypothalamic Neurons", Current Protocols in Neuroscience, Oct. 24, 2017, pp. 3.33.1-3.33.24. (cited in the Jul. 29, 2019 Search Report issued for the European patent application No. 17 74 1428.1).

Liheng Wang et al., "Efficient Generation of Hypothalamic Neurons from Human Pluripotent Stem Cells" Current Protocols in Human Genetics, Jul. 1, 2017, pp. 21.5.1-21.5.14. (cited in the Jul. 29, 2019 Search Report issued for the European patent application No. 17 74 1428.1).

Supplementary European Search Report mailed Jul. 29, 2019, issued for the European patent application No. 17 74 1428.1.

Search Report and Written Opinion dated Nov. 28, 2019, issued for the corresponding Singapore patent application No. 11201806557V.

H. Suga et al., "Self-formation of functional adeno-hypophysis in three-dimensional culture," doi:10.1038/nature10637, vol. 480, Dec. 1, 2011, pp. 57-64.

Nature 2011, "Supplementary Information"; Research Supplementary Information; doi:10.1038/nature10637; 2011, pp. 1-14.

* cited by examiner

Ventral hypothalamic induction

Dissociation medium: DFNB, CNTF (10 ng/ml), BDNF (50 ng/ml), NT3 (50 ng/ml), FBS (10% of the total volume in volume ratio)

DFNB: DMEM/F12 (7g/l of glucose, N2 supplement, added B27 supplement)

Coating agent: Matrigel, PDL, laminin

ACTH stimulation test by CRH

Add 5 μg/ml of CRH

\* $p<0.05$

ACTH positive cells are CRH-R1 positive

Day 60

DIFFERENTIATION INDUCTION FROM HUMAN PLURIPOTENT STEM CELLS INTO HYPOTHALAMIC NEURONS

TECHNICAL FIELD

The present invention relates to a technique of differentiating human pluripotent stem cells into hypothalamic neurons and its application. This application claims priority based on Japanese Patent Application No. 2016-10940 filed on Jan. 22, 2016, the entire contents of which are incorporated herein by reference.

BACKGROUND ART

Hypothalamus is the center for maintaining homeostasis of the human body, such as growth, puberty, metabolism, stress response, reproduction, nursing care, and immunity. Especially recently, interest in appetite control associated with the increase of lifestyle diseases such as diabetes is increasing, and the appetite center also exists in hypothalamus. Besides, there have been increasing reports that oxytocin, which is one of the hypothalamic hormones, is involved in the relationship of trust and affection, in addition to the conventionally known milk ejection/uterine contraction effect, and oxytocin has proved to be a hormone deeply involved in human life.

When hypothalamus develops abnormality, normal hormone secretion does not take place, so that diseases such as central diabetes insipidus, eating disorders, sleeping disorders, etc. are caused. Hormone replacement therapy is performed against insufficient hormone secretion caused by hypothalamic abnormality. However, there are limitations to hormone replacement therapy, and sufficient effects are not obtained in many cases. Originally, the amount of hormone to be secreted is regulated in response to changes in the environment. It can be said to be practically impossible to reproduce such a regulating mechanism of organisms by hormone replacement from the external.

Since hypothalamus is located in a deep part of the brain and is a small region, it was difficult to extract an actual tissue and use it for research. On the other hand, attempts have been made to prepare hypothalamic neurons from pluripotent stem cells such as ES cells. For example, in 2008, Wataya et al. developed a SFEBq method and established a technique for differentiation induction from mouse ES cells into hypothalamic AVP-producing cells (Non-Patent Literature 1). In the SFEBq method, a gfCDM medium free from serum or growth factors is used to aggregate cells in a non-adhesive plate and perform three-dimensional suspension culture, thereby differentiating into nerve tissue. In 2015, Merkle et al. succeeded in differentiation induction of hypothalamic neurons from human ES cells and iPS cells using two methods of three-dimensional suspension culture and two-dimensional plane culture (Non-Patent Literature 2).

CITATION LIST

Non-Patent Literature

Non Patent Literature 1: Wataya T. et al., Minimization of exogenous signals in ES cell culture induces rostral hypothalamic differentiation. Proc Natl Acad Sci USA 105(33): 11796-11801 (2008)

Non Patent Literature 2: Merkle F T et al., Generation of neuropeptidergic hypothalamic neurons from human pluripotent stem cells. Development. 2015 Feb. 15; 142 (4):633-43

Non Patent Literature 3: Ozone C et al., Functional anterior pituitary generated in self-organizing culture of human embryonic stem cells. Nat Commun. 2016 Jan. 14; 7: 10351

SUMMARY OF INVENTION

Technical Problem

As described above, attempts have been made to induce differentiation of pluripotent stem cells into hypothalamic neurons. However, the method of Wataya et al. did not succeed in differentiation of human ES cells. In addition, in the method of Merkle et al., the AVP differentiation efficiency is very poor (differentiation efficiency is about 0.2%) in three-dimensional culture, and there is no successful differentiation into AVP neurons in two-dimensional culture.

If a method for differentiation induction of human pluripotent stem cells (ES cells and iPS cells) into hypothalamic neurons, in other words, a method for constructing hypothalamic tissue can be established, the development of a treatment method for hypothalamic disorders will be greatly advanced. For example, it becomes possible to analyze pathology and develop treatment methods using disease-specific iPS cells established from patients with central diabetes insipidus. Such a method can also be applied to a transplantation therapy.

On the other hand, since hypothalamus and pituitary are originally functionally inseparable, a structure in which hypothalamus and pituitary are functionally integrated is an extremely effective tool, for example, for drug screening targeting hypothalamus and/or pituitary. In addition, the structure is highly useful also as an implant material against hypothalamic and/or pituitary dysfunction.

Under the above background, a first object of the present invention is to provide a method for efficient differentiation induction of human pluripotent stem cells into hypothalamic neurons. A second object of the invention is to provide a method for constructing a cellular structure in which hypothalamic tissue and pituitary tissue are integrated from human pluripotent stem cells.

Solution to Problem

The present inventors have earnestly studied to solve the above problems. First, the method of Merkle et al. was not necessarily a differentiation method according to the order of development, and it was thought that human pluripotent stem cells were differentiated into the ventral side in hypothalamus, based on inference from their results. Generally, AVP neurons are found on the dorsal hypothalamus. Therefore, the present inventors considered that by searching for and optimizing the differentiation conditions for sequentially reproducing the respective stages of development, the induction position in hypothalamus was more precisely regulated, and, as a result, AVP neurons of the dorsal hypothalamus could be obtained. Rx (retina and anterior neural fold homeobox) which is an initial hypothalamic marker, Pax6 (paired box 6) which is a dorsal side marker, and Otp (orthopedia homeobox) and Brn2 (also known as POU3F2, POU class 3 homeobox 2, etc.) Which are Bona ride markers of AVP, and, lastly, AVP were used as markers for the respective differentiation steps.

First, when the inventors attempted differentiation using a growth-factor-free Chemically Defined Medium (gfCDM) alone, in accordance with the method of Wataya et al. (Non-Patent Literature 1), cells did not successfully form an aggregate. The inventors considered that this unsuccess was caused by nutritional deficiency, and, therefore, added a small amount of a serum alternative KSR to the medium. So, an aggregate could be formed, but the positional information was shifted to the telencephalon. Next, when a BMP4 signal was added, Rx as a hypothalamus marker and Pax6 as a dorsal marker became co-positive, but it was found that the retinal marker Chx10 also became positive and that the cells were differentiated into neural retinas. Then, when the Shh (Sonic hedgehog) signal (SAG which is a Shh agonist) of the ventralization factor was added, it became possible to differentiate into hypothalamic precursor cells.

As a result of further study, the dorsal hypothalamus and the ventral hypothalamus was successfully separately produced, by adjusting the concentration of KSR and the concentrations of the BMP4 signal and the Shh signal (SAG) and by adding or not adding a small amount of an Akt inhibitor which is another ventralization signal. That is, dorsal hypothalamic induction conditions and ventral hypothalamic induction conditions were found. As a result of continued suspension culture under the dorsal hypothalamus induction conditions, the expression of Otp and Brn2 was confirmed, and the expression of AVP was confirmed on Day 100 of culture, but the number thereof was small. Therefore, when dissociation culture, which is considered to be advantageous in neurogenesis, was incorporated, the appearance of AVP neurons was confirmed on Day 150 of culture. The inventors also confirmed that the AVP neurons actually secreted AVP hormone. In addition, AVP neurons showed good reactivity in stimulation tests.

It was confirmed that when the cells were cultured under the dorsal hypothalamic induction conditions or the ventral hypothalamic induction conditions, the differentiation thereof into hypothalamic neurons other than AVP neurons could be induced. When the culture was continued under the ventral hypothalamus induction conditions, ventral hypothalamic neurons such as MCH neurons were observed at a rate higher than that under the dorsal hypothalamic induction conditions.

On the other hand, the inventors succeeded in differentiating into and maturing both hypothalamus and pituitary from one cell aggregate by combining the hypothalamic neuron maturation condition (use of a medium for dissociation culture) and adjusting the conditions for the respective stages.

As described above, as a result of this study, it became possible to induce differentiation into hypothalamic neurons (e.g., AVP neurons) at a higher rate as compared with that in the method of Merkle et al. In addition, it became possible to exactly separately produce the dorsal hypothalamus and the ventral hypothalamus, with the result that it has become possible to more precisely regulate the differentiation induction itself. The differentiation of oxytocin-producing neurons, also called love hormone, and a plurality of hypothalamic hormone-producing neurons related to appetite, in addition to AVP neurons, could also be induced. Furthermore, the inventors successfully constructed a structure in which hypothalamus and pituitary were functionally integrated.

The following inventions are mainly based on the above results.

[1] A method for producing a cellular structure including hypothalamic tissue, the method including the steps of:

(1) culturing an aggregate of human pluripotent stem cells in suspension in a medium containing a low concentration of a bone morphogenetic protein signal transduction pathway activating substance and a low concentration of a substance acting on the Shh signaling pathway, and (2) further culturing the cell aggregate obtained in the step (1) in suspension in a medium containing a low concentration of a substance acting on the Shh signaling pathway.

[2] The producing method according to [1], wherein the step (2) is carried out under a high oxygen partial pressure condition.

[3] The producing method according to [1] or [2], further including the step of: (3) recovering the cell aggregate obtained in the step (2) and subjecting the cells constituting the cell aggregate to dissociation culture.

[4] The producing method according to [3], wherein the step (3) is carried out under a high oxygen partial pressure condition.

[5] The producing method according to any one of [1] to [4],
wherein the bone morphogenetic protein signal transduction pathway activating substance in the step (1) is BMP4, and the concentration thereof in the medium is 0.1 nM to 5.0 nM,
wherein the substance acting on the Shh signaling pathway in the steps (1) and (2) is SAG, and the concentration thereof in the medium is 0.1 μM to 2.0 μM, and
wherein the differentiation into dorsal hypothalamic tissue is induced by the steps (1) and (2).

[6] The producing method according to [5], wherein the dorsal hypothalamic tissue includes one or more neurons selected from the group consisting of vasopressin neurons, oxytocin neurons, thyrotropin releasing hormone neurons, corticotropin releasing hormone neurons and neuropeptide Y neurons.

[7] The producing method according to any one of [1] to [4],
wherein the bone morphogenetic protein signal transduction pathway activating substance in the step (1) is BMP4, and the concentration thereof in the medium is 0.1 nM to 3.0 nM,
wherein the substance acting on the Shh signaling pathway in the steps (1) and (2) is SAG, and the concentration thereof in the medium is 0.1 μM to 2.0 μM,
wherein the medium further includes an Akt inhibitor, and
wherein the differentiation into ventral hypothalamic tissue is induced by the steps (1) and (2).

[8] The producing method according to [7], wherein the ventral hypothalamic tissue includes one or more neurons selected from the group consisting of agouti-related protein neurons, proopiomelanocortin neurons, melanin-concentrating hormone neurons and Orexin neurons.

[9] The producing method according to any one of [1] to [8], wherein the suspension culture is carried out in the absence of feeder cells.

[10] The producing method according to any one of [1] to [9], wherein the aggregate in the step (1) is formed by culturing dispersed human pluripotent stem cells in suspension.

[11] The producing method according to [10], wherein the suspension culture is carried out by SFEBq (Serum-free Floating culture of Embryoid Body-like aggregates with quick reaggregation) method.

[12] A method for producing a cellular structure including hypothalamic tissue and pituitary tissue, the method including the steps of:
(i) culturing an aggregate of human pluripotent stem cells in suspension in a medium containing a bone morphogenetic protein signal transduction pathway activating substance and a substance acting on the Shh signaling pathway,
(ii) further culturing the cell aggregate formed in the step (i) in suspension in a medium containing a bone morphogenetic protein signal transduction pathway activating substance and a substance acting on the Shh signaling pathway, and
(iii) culturing the cell aggregate obtained in the step (ii) in suspension in a medium suitable for simultaneous induction of pituitary and hypothalamus.

[13] The producing method according to [12], wherein the steps (ii) and (iii) are carried out under a high oxygen partial pressure condition.

[14] The producing method according to [12] or [13], wherein the following step (a) is performed between the steps (ii) and (iii), and wherein, in the step (iii), the cell aggregate obtained in the step (a) is cultured in suspension:
(a) further culturing the cell aggregate obtained in the step (ii) in suspension in a medium containing the substance acting on the Shh signaling pathway.

[15] The producing method according to any one of [12] to [14], wherein the step (a) is carried out under a high oxygen partial pressure condition.

[16] The producing method according to any one of [12] to [15], wherein the suspension culture is carried out in the absence of feeder cells.

[17] The producing method according to any one of [12] to [16], wherein the aggregate in the step (i) is formed by culturing dispersed human pluripotent stem cells in suspension.

[18] The producing method according to any one of [12] to [17], wherein the bone morphogenetic protein signal transduction pathway activating substance is BMP4.

[19] The producing method according to any one of [12 to [18], wherein the substance acting on the Shh signaling pathway is SAG.

[20] A cellular structure obtained by the producing method according to any one of [1] to [19].

DESCRIPTION OF EMBODIMENTS

Figure 1:
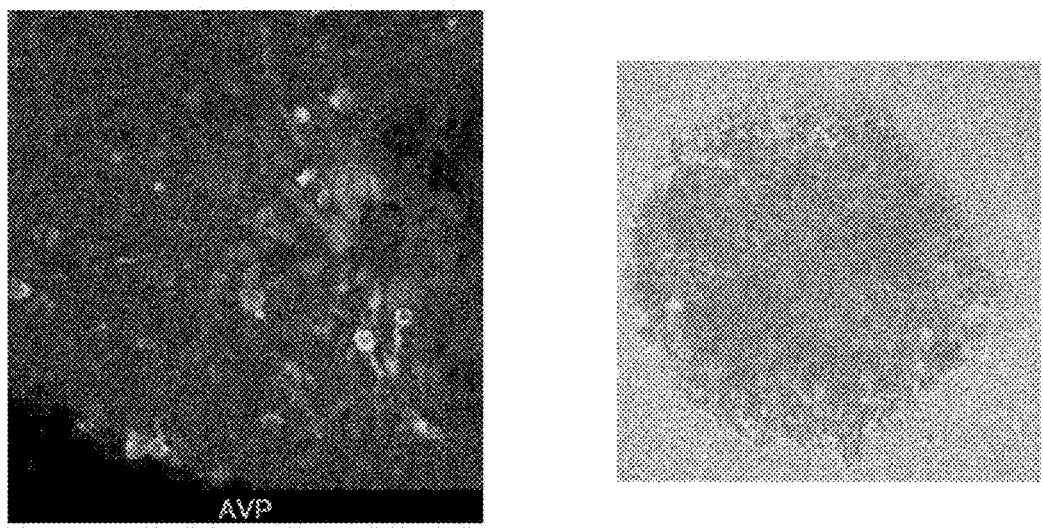
FIG. 1 shows differentiation of mouse ES cells into AVP neurons (left) and culture results of human ES cells (right). No cell aggregate was formed when a differentiation method effective for mouse ES cells was applied to human ES cells. AVP: Green.

1. Method for Producing Cellular Structure Including Hypothalamic Tissue

A first aspect of the present invention relates to a method for producing a cellular structure comprising a hypothalamic tissue. Hypothalamus is composed of arcuate nucleus, paraventricular nucleus, periventricular nucleus, supraoptic nucleus, preoptic nucleus, dorsomedial hypothalamic nucleus, ventromedial hypothalamic nucleus, posterior nucleus, and the like. In hypothalamus, there is a group of cells having the functions of nerve cells and endocrine cells in combination. From the positional relationship, hypothalamus can be roughly divided into the dorsal hypothalamus and the ventral hypothalamus. Characteristic nerve cells (hypothalamic neurons) exist in the dorsal hypothalamus and the ventral hypothalamus, respectively. In hypothalamus, examples of the nerve cells observed to be mainly localized near the dorsal side include vasopressin (AVP) neurons, oxytocin (OXT) neurons, thyrotropin releasing hormone (TRH) neurons, corticotropin releasing hormone (CRH) neurons, and neuropeptide Y (NPY) neurons, and examples of the nerve cells observed to be mainly localized near the ventral side include agouti-related protein (AgRP) neurons, proopiomelanocortin (POMC) neurons, melanin concentrating hormone (MCH) neurons, and Orexin neurons.

In the present invention, "hypothalamic tissue" is used as a term generically referring to the dorsal hypothalamus and the ventral hypothalamus. Thus, unless otherwise noted, the term "hypothalamic tissue" means the dorsal hypothalamus or the ventral hypothalamus, or a tissue including both of them.

In the producing method of the present invention, the following the steps (1) and (2) are performed:
(1) culturing an aggregate of human pluripotent stem cells in suspension in a medium containing a low concentration of a bone morphogenetic protein signal transduction pathway activating substance and a low concentration of a substance acting on the Shh signaling pathway, and
(2) further culturing the cell aggregate obtained in the step (1) in suspension in a medium containing a low concentration of a substance acting on the Shh signaling pathway.

Step (1)

In step (1), first, human pluripotent stem cell aggregates are used. The "human pluripotent stem cell" refers to a human cell having both the potential for differentiating into all cells constituting the body (pluripotency), and the potential for producing daughter cells having the same differentiation potency via cell division (self-replication competence). The pluripotency can be evaluated by transplanting cells of an evaluation subject into a nude mouse, and testing the presence or absence of formation of teratoma containing each cell of the three germ layers (ectoderm, mesoderm, and endoderm).

Examples of the pluripotent stem cells include embryonic stem cells (ES cells), embryonic germ cells (EG cells), and induced pluripotent stem cells (iPS cells), but the cells are not limited thereto as long as they have both the pluripotency and the self-replication competence. In the present invention, ES cells or iPS cells are preferably used.

ES cells can be established by culturing, for example, a pre-implantation early embryo, an inner cell mass that constitutes the early embryo, a single blastomere, and the like (Manipulating the Mouse Embryo A Laboratory Manual, Second Edition, Cold Spring Harbor Laboratory Press (1994); Thomson, J A et al., Science, 282, 1145-1147 (1998)). As the early embryo, an early embryo prepared by nuclear-transplanting the nucleus of a somatic cell may be used (Wilmut et al. (Nature, 385, 810 (1997)), Cibelli et al. (Science, 280, 1256 (Nature, 394, 369 (1998)), Akira IRI-TANI et al. (Tanpakushitsu Kakusan Koso, 44, 892 (1999)), Baguisi et al. (Nature Biotechnology, 17, 456 (1999)), Wakayama et al. (Nature, 394, 369 (1998); Nature Genetics, 22, 127 (1999); Proc. Natl. Acad. Sci. USA, 96, 14984 (1999)), Rideout III et al. (Nature Genetics, 24, 109 (2000), Tachibana et al. Human Embryonic Stem Cells Derived by Somatic Cell Nuclear Transfer, Cell (2013) in press). As an early embryo, a parthenogenetic embryo may also be used: Kim et al. (Science, 315, 482-486 (2007)), Nakajima et al. (Stem Cells, 25, 983-985 (2007)), Kim et al. (Cell Stem Cell, 1, 346-352 (2007)), Revazova et al. (Cloning Stem Cells, 9, 432-449 (2007)), Revazova et al. (Cloning Stem Cells, 10, 11-24 (2008)). In addition to the above-mentioned papers, Stregkchenko N., et al. Reprod Biomed Online. 9: 623-629, 2004; Klimanskaya I., et al. Nature 444: 481-485, 2006; Chung Y., et al. Cell Stem Cell 2: 113-117, 2008; Zhang X., et al. Stem Cells 24: 2669-2676, 2006; Wassarman, P. M. et al. Methods in Enzymology, Vol. 365, 2003, etc. may also be referred to, as for the preparation of ES cells. Fused ES cells obtained by cell fusion of ES cells and somatic cells are also included in the embryonic stem cells used for the method of the present invention.

Some ES cells are available from preservation institutes or commercially available. For example, human ES cells are available from the Institute for Frontier Medical Sciences, Kyoto University (for example, KhES-1, KhES-2, and KhES-3), WiCell Research Institute, ESI BIO, and the like.

EG cells can be established by culturing primordial germ cells in the presence of LIF, bFGF, SCF, and the like (Matsui et al., Cell, 70, 841-847 (1992), Shamblott et al., Proc. Natl. Acad. Sci. USA, 95 (23), 13726-13731 (1998), Turnpenny et al., Stem Cells, 21 (5), 598-609, (2003)).

The "induced pluripotent stem cell (iPS cell)" refers to a cell having pluripotency and self-replication competence, produced by reprogramming somatic cells (e.g., fibroblasts, skin cells, and lymphocytes), for example, through the introduction of initializing factors. iPS cells show characteristics similar to those of ES cells. Somatic cells used in the preparation of iPS cells are not particularly limited, and may be differentiated somatic cells or undifferentiated stem cells. iPS cells can be prepared by various methods reported so far. The application of iPS cell preparation methods which will be developed in the future is also contemplated.

The most fundamental technique of iPS cell preparation methods is to introduce four factors of Oct3/4, Sox2, Klf4, and c-Myc, which are transcription factors, into cells by using virus (Takahashi K, Yamanaka S: Cell 126 (4), 663-676, 2006; Takahashi, K, et al.: Cell 131 (5), 861-72, 2007). The establishment of human iPS cells by introduction of four factors of Oct4, Sox2, Lin28, and Nonog has been reported (Yu J, et al.: Science 318 (5858), 1917-1920, 2007). The establishment of iPS cells by introduction of three factors other than c-Myc (Nakagawa M, et al.: Nat. Biotechnol. 26 (1), 101-106, 2008), two factors of Oct3/4 and Klf4 (Kim J B, et al.: Nature 454 (7204), 646-650, 2008), or only Oct3/4 (Kim J B, et al.: Cell 136 (3), 411-419, 2009) has also been reported. Also, a technique for introducing a protein, which is an expression product of a gene, into cells (Thou H, Wu S, Joo J Y, et al.: Cell Stem Cell 4, 381-384, 2009; Kim D, Kim C H, Moon J I, et al: Cell Stem Cell 4, 472-476, 2009) has also been reported. On the other hand, it has been reported that it is possible to improve the preparation efficiency and reduce the factors to be introduced, by using, for example, an inhibitor BIX-01294 against histone methyltransferase G9a, a histone deacetylase inhibitor valproic acid (VPA), or BayK8644 (Huangfu D, et al.: Nat. Biotechnol. 26 (7), 795-797, 2008; Huangfu D, et al.: Nat. Biotechnol. 26 (11), 1269-1275, 2008; Silva J, et al.: PLoS. Biol. 6 (10), e 253, 2008). Studies have also been advanced on gene transfer methods, and techniques utilizing not only retroviruses, but also lentiviruses (Yu J, et al.: Science 318 (5858), 1917-1920, 2007), adenoviruses (Stadtfeld M, et al.: Science 322 (5903), 945-949, 2008), plasmids (Okita K, et al.: Science 322 (5903), 949-953, 2008), transposon vectors (Woltjen K, Michael I P, Mohseni P, et al.: Nature 458, 766-770, 2009; Kaji K, Norrby K, Pac a A, et al.: Nature 458, 771-775, 2009; Yusa K, Rad R, Takeda J, et al.: Nat Methods 6, 363-369, 2009), or episomal vectors (Yu J, Hu K, Smuga-Otto K, Tian S, et al: Science 324, 797-801, 2009) for gene transfer have been developed.

Cells in which transformation into iPS cells, i.e., initialization (reprogramming) has occurred can be selected by using, as an indicator, the expression of pluripotent stem cell markers (undifferentiated markers) such as Fbxo15, Nanog, Oct/4, Fgf-4, Esg-1, and Cript.

iPS cells can also be provided from, for example, the National University Corporation, Kyoto University or the Independent Administrative Institution, RIKEN BioResource Center.

Human pluripotent stem cells can be maintained in vitro by known methods. For example, when it is desired to provide highly safe cells (e.g. in a case where clinical application is considered), pluripotent stem cells are preferably maintained by serum-free culture using a serum alternative (such as Knockout serum replacement (KSR)) or by feeder-free cell culture. If a serum is used (or used in combination), autologous serum (i.e., recipient's serum) is preferably used.

The "aggregate of human pluripotent stem cell" used in the step (1) can be obtained by culturing dispersed human pluripotent stem cells under conditions that are non-adhesive to a culture vessel (that is, culturing in suspension) and assembling a plurality of human pluripotent stem cells to allow for aggregate formation.

A culture vessel used for aggregate formation is not particularly limited. For example, flasks, tissue culture flasks, dishes, Petri dishes, tissue culture dishes, multidishes, microplates, microwell plates, micropores, multiplates, multi-well plates, chamber slides, laboratory dishes, tubes, trays, culture bags, roller bottles, and the like can be used. In order to enable culture under non-adhesive conditions, it is preferable to use a culture vessel having a non-cell-adherent culture surface. Examples of the culture vessel involved include culture vessels whose surfaces (culture surfaces) have been treated to be non-cell-adherent, and culture vessels whose surfaces (culture surfaces) have not undergone a treatment for improving the cell adhesiveness (for example, coating treatment with an extracellular matrix).

The medium to be used for aggregate formation can be prepared using a medium used for culturing mammalian cells as a basal medium. As the basal medium, for example, a BME medium, a BGJb medium, a CMRL 1066 medium, a Glasgow MEM medium, an Improved MEM Zinc Option medium, an IMDM medium, a Medium 199 medium, an Eagle MEM medium, an αMEM medium, a DMEM medium, a Ham's medium, a Ham's F-12 medium, a RPMI 1640 medium, a Fischer's medium, a Neurobasal medium, and a mixed medium thereof can be used, and the basal medium is not particularly limited as long as the it can be used for culturing mammalian cells. In one embodiment, a mixed medium of IMDM medium and Ham's F-12 medium is used. The mixing ratio is, for example, IMDM: Ham's F-12=0.8 to 1.2:1.2 to 0.8 in a volume ratio.

Either a serum-containing medium or a serum-free medium can be used. A serum-free medium is a medium containing no serum. A medium containing purified components derived from blood and components derived from animal tissues (e.g., growth factor) is a serum-free medium as long as it does not contain a serum itself. In order to avoid contamination with unknown or unintended components, it is preferable to use a serum-free medium.

The medium to be used for aggregate formation may contain a serum alternative. The serum alternative may contain, for example, albumin, transferrin, a fatty acid, a collagen precursor, a trace element, 2-mercaptoethanol or 3' thiol glycerol, or an equivalent thereof. A serum alternative can be prepared by known methods (see, for example, WO 98/30679). Commercially available serum alternatives can also be used. Examples of the commercially available serum alternatives include KSR (manufactured by Invitrogen), Chemically-defined Lipid concentrated (manufactured by Gibco), and Glutamax (manufactured by Gibco).

The medium used for aggregate formation can contain other additives on the condition that the induction of differentiation from human pluripotent stem cells into a target tissue is not adversely affected. Examples of the additives include insulin, an iron source (e.g., transferrin), a mineral (e.g., sodium selenate), a saccharide (e.g., glucose), an organic acid (e.g., pyruvic acid or lactic acid), a serum protein (e.g., albumin), an amino acid (e.g., L-glutamine), a reducing agent (e.g., 2-mercaptoethanol), a vitamin (e.g., ascorbic acid or d-biotin), an antibiotic (e.g., streptomycin, penicillin or gentamicin), and a buffer (e.g., HEPES).

For example, for formation of an aggregate of human pluripotent stem cells, human pluripotent stem cells are first collected from a passage culture, and dispersed to single cell state or a state close thereto. Human pluripotent stem cells can be dispersed using an appropriate cell dissociation solution. As the cell dissociation solution, for example, protease such as EDTA-trypsin and collagenase IV, metalloprotease can be used alone or in an appropriate combination. Cell dissociating solutions with low cell toxicity are preferred. As such cell dissociation solutions, commercially available products such as DISPASE (EIDIA Co., Ltd.), TrypLE (Invitrogen) or Accutase (MILLIPORE) are available. The dispersed human pluripotent stem cells are suspended in the medium described above.

A suspension of the dispersed human pluripotent stem cells is seeded in the culture vessel and the dispersed human pluripotent stem cells are cultured under conditions that are non-adhesive to the culture vessel, whereby a plurality of human pluripotent stem cells are assembled to form an aggregate. In this case, the dispersed human pluripotent stem cells may be seeded in a relatively large culture vessel (for example, 10-cm dish) to simultaneously form a plurality of human pluripotent stem cell aggregates in one culture compartment, but, in such simultaneous formation, the size of aggregates, and the number of human pluripotent stem cells contained therein can widely vary. Then, this variation may cause a difference in the level of differentiation among the cell aggregates, and, as a result, the differentiation induction efficiency decreases. Therefore, it is preferable to rapidly aggregate the dispersed human pluripotent stem cells to form one aggregate in one culture compartment. As a method for rapidly aggregating the dispersed human pluripotent stem cells, for example, the following methods (1) and (2) can be employed.

(1) The dispersed human pluripotent stem cells are enclosed in a culture compartment having a relatively small volume (e.g., 1 ml or less, 500 μl or less, 200 μl or less, 100 μl or less) to form one aggregate in the compartment. Preferably, after enclosing the dispersed human pluripotent stem cells, the culture compartment is stood still. Examples of the culture compartment include, but are not limited to, a well in a multi-well plate (384-well, 192-well, 96-well, 48-well, 24-well, etc.), micropore, chamber slide, and the like, tube, and a droplet of a medium in hanging drop method. The dispersed human pluripotent stem cells enclosed in the compartment are precipitated on one spot by the action of gravity or the cells adhere to each other to form one aggregate in one compartment. The shape of the bottom of the multi-well plate, micropore, chamber slide, tube or the like is preferably U-bottom or V-bottom to facilitate precipitation of the dispersed human pluripotent stem cells on one spot.

(2) The dispersed human pluripotent stem cells are placed in a centrifuge tube and centrifuged to precipitate human pluripotent stem cells on one spot. One aggregate is formed in the tube.

The number of human pluripotent stem cells to be seeded in one culture compartment is not particularly limited as long as one aggregate is formed per culture compartment, and differentiation from human pluripotent stem cells into target tissues (hypothalamic tissue, i.e., hypothalamus and pituitary tissue) can be induced in the aggregate by the method of the invention, but usually, about $1 \times 10^3$ to about $5 \times 10^4$, preferably about $1 \times 10^3$ to about $2 \times 10^4$, more preferably about $2 \times 10^3$ to about $1.2 \times 10^4$ human pluripotent stem cells are seeded per culture compartment. By rapidly aggregating human pluripotent stem cells, one cell aggregate usually composed of about $1 \times 10^3$ to about $5 \times 10^4$, preferably about $1 \times 10^3$ to about $2 \times 10^4$, more preferably about $2 \times 10^3$ to about $1.2 \times 10^4$ human pluripotent stem cells is formed per culture compartment.

The time until aggregate formation can be appropriately determined within a range where one aggregate is formed per culture compartment and the differentiation from human pluripotent stem cells to the target tissues can be induced in the aggregate by the method of the present invention, but is preferably short in order to efficiently induce differentiation into the target tissues. Preferably, a human pluripotent stem cell aggregate is formed within 24 hours, more preferably within 12 hours, more preferably within 6 hours, most preferably 2 to 3 hours. Those skilled in the art can appropriately adjust the time until aggregate formation by setting or adjusting instruments and conditions (for example, conditions of centrifuge) for cell aggregation.

Other culture conditions such as culture temperature and $CO_2$ concentration at the time of aggregate formation can be set as appropriate. The culture temperature is not particularly limited, but is, for example, about 30 to 40° C., preferably about 37° C. The $CO_2$ concentration is, for example, about 1 to 10%, preferably about 5%.

A qualitatively uniform population of human pluripotent stem cell aggregates can be obtained by preparing a plurality of culture compartments under the same culture conditions and forming one human pluripotent stem cell aggregate in each culture compartment. Whether human pluripotent stem cell aggregates are qualitatively uniform can be evaluated based on the size of the aggregate and the number of cells therein, macroscopic morphology, microscopic morphology and homogeneity thereof by histological staining analysis, expression of differentiation and un-differentiation markers and homogeneity thereof, regulation of the expression of differentiation markers and synchronicity thereof, reproducibility of differentiation efficiency among aggregates, and the like. In one embodiment, the population of human pluripotent stem cell aggregates for use in the method of the present invention contains a uniform number of human pluripotent stem cells in the aggregates. For a particular parameter, a population of human pluripotent stem cell aggregates being "uniform" means that 90% or more of the cell aggregates in the entire population thereof falls within the range of average of the parameter in the aggregate population ±10%, preferably ±5%.

In the step (1), an aggregate of human pluripotent stem cells is cultured in suspension in a medium containing a low concentration of a bone morphogenetic protein signal transduction pathway activating substance and a low concentration of a substance acting on the Shh signaling pathway.

The phrase "culturing in suspension" of an aggregate refers to culturing an aggregate in a medium under conditions that are non-adhesive to the culture vessel. A medium to be used in suspension culture contains a low concentration of a bone morphogenetic protein signal transduction pathway activating substance and a low concentration of a substance acting on the Shh signaling pathway. Differentiation of human pluripotent stem cells into hypothalamus is induced by the actions of the bone morphogenetic protein signal transduction pathway activating substance and the substance acting on the Shh signaling pathway.

The culture vessel to be used in suspension culture is not particularly limited. For example, flasks, tissue culture flasks, dishes, Petri dishes, tissue culture dishes, multi-dishes, microplates, microwell plates, micropores, multi-plates, multi-well plates, chamber slides, laboratory dishes, tubes, trays, culture bags, roller bottles, and the like can be used. In order to enable culture under non-adhesive conditions, it is preferable to use a culture vessel having a non-cell-adherent culture surface. Examples of the culture vessel involved include culture vessels whose surfaces (culture surfaces) have been treated to be non-cell-adherent, and culture vessels whose surfaces (culture surfaces) have not undergone a treatment for improving the cell adhesiveness (for example, coating treatment with an extracellular matrix).

As the culture vessel used in the suspension culture, an oxygen permeable culture vessel may be used. By using an oxygen permeable culture vessel, the supply of oxygen to cell aggregates can be improved, which can contribute to the long-term maintenance culture of the cell aggregates.

In the suspension culture of the cell aggregates, the cell aggregates may be either statically cultured or consciously moved by gyratory culture or shake culture, as long as the non-adherent state of the cell aggregates to the culture vessel can be maintained. However, in the present invention, it is unnecessary to consciously move the aggregates by gyratory culture or shake culture. That is, in one embodiment, the suspension culture in the producing method of the present invention is carried out by static culture. The "static culture" refers to a culture method in which aggregates are cultured in a state in which they are not consciously moved. For example, the medium is convected along with local changes in temperature of the medium, and the aggregates may be moved by the convection flow. But, since the aggregates are not consciously moved, the culture in such a case also corresponds to static culture. Static culture may be carried out throughout the whole period of suspension culture or only for a part of the period. In a preferred embodiment, static culture is carried out throughout the whole period of suspension culture. Static culture has many advantages, for example, that no special device is needed; that the cell aggregates are expected to be less damaged; and that the amount of the culture solution can be reduced.

The suspension culture of the cell aggregates may be performed under either condition, i.e., in the presence/absence of feeder cells, but is preferably performed in the absence of feeder cells from the viewpoint of avoiding contamination of undetermined factors.

The other culture conditions such as the culture temperature, $CO_2$ concentration, and $O_2$ concentration in the suspension culture of the cell aggregates can be set appropriately. The culture temperature is, for example, about 30 to 40° C., preferably about 37° C. The $CO_2$ concentration is, for example, about 1 to 10%, preferably about 5%. The $O_2$ concentration is, for example, about 20%.

In the present invention, the "bone morphogenetic protein signal transduction pathway activating substance" means a substance which activates a pathway through which a signal is transmitted by binding of a bone morphogenetic factor and a receptor. Examples of the bone morphogenetic protein signal transduction pathway activating substance include BMP2, BMP4, BMP7 and GDF5. Preferably, BMP4 is used as the bone morphogenetic protein signal transduction pathway activating substance. BMP4 will be mainly described below, but the bone morphogenetic protein signal transduction pathway activating substance used in the present invention is not limited to BMP4. BMP4 is a known cytokine and the amino acid sequence thereof is also known. BMP4 to be used in the present invention is mammalian BMP4. Examples of the mammals include experiment animals such as rodents such as mice, rats, hamsters and guinea pigs, and the like, rabbits and the like; domestic animals such as swines, bovines, goats, horses and sheep; companion animals such as dogs and cats; and primates such as humans, monkeys, orangutans and chimpanzees. BMP4 is preferably BMP4 of rodents (for example, mouse or rat) or a primate (human, etc.), most preferably human BMP4. The "human BMP4" means BMP4 having an amino acid sequence of BMP4 naturally expressed in the human body. As representative amino acid sequences of human BMP4, NCBI accession numbers, NP-001193.2 (updated on Jun. 15, 2013), NP-570911.2 (updated on Jun. 15, 2013), and NP-570912.2 (updated on Jun. 15, 2013), and amino acid sequences (mature human BMP4 amino acid sequences) obtained by removing the N-terminal signal sequence (1-24) from each of these amino acid sequences can be exemplified.

The substance acting on the Shh signaling pathway in the present invention is not particularly limited as long as it can enhance Shh-mediated signal transduction. Examples of the substance acting on the Shh signaling pathway include proteins belonging to the Hedgehog family (e.g., Shh), Shh receptors, Shh receptor agonists, Purmorphamine, Smoothened Agonist (SAG) (3-Chloro-N-[trans-4-methylamino)cyclohexyl]-N-[[3-(4-pyridinyl)phenyl]methyl]-benzo[b]thiophene-2-carboxamide) and Hh-Ag 1.5(3-chloro-4,7-difluoro-(4-(methylamino)cyclohexyl)-N-(3(pyfidin-4-yl) benzyl)benzo[b]thiophene-2-carboxamide. SAG is particularly preferred.

A preferable combination of a bone morphogenetic protein signal transduction pathway activating substance and substance acting on the Shh signaling pathway is a combination of BMP4 and SAG.

In the present invention, in order to induce differentiation into hypothalamic tissue, a medium containing a low concentration of a bone morphogenetic protein signal transduction pathway activating substance and a low concentration of a substance acting on the Shh signaling pathway is used. In one embodiment (hereinafter referred to as "first embodiment"), the differentiation into the dorsal hypothalamic tissue is induced. In this embodiment, the "low concentration" when BMP4 is used as the bone morphogenetic protein signal transduction pathway activating substance is, for example, 0.1 nM to 5.0 nM, preferably 0.5 nM to 4.0 nM, more preferably 1.0 nM to 3.0 nM. The concentration of the bone morphogenetic protein signal transduction pathway activating substance may not be constant over the entire period of the step (1). For example, the bone morphogenetic protein signal transduction pathway activating substance may not be added to the medium for 3 to 8 days (6 days as a specific example) from the beginning of the suspension culture, and then added thereto. The concentration of the bone morphogenetic protein signal transduction pathway activating substance may be reduced during the culture. For example, the bone morphogenetic protein signal transduction pathway activating substance is not added to the medium for 3 to 8 days (6 days as a specific example) from the beginning of the suspension culture, and the culture is performed under the condition where the concentration of the bone morphogenetic protein signal transduction pathway activating substance in the medium is relatively high (for example, using a medium containing BMP4 at a concentration of 1.0 nM to 3.0 nM) for the subsequent 6 to 12 days (9 days as a specific example). For the subsequent 1 to 5 days (3 days as a specific example), the culture was performed under the condition where the concentration of the bone morphogenetic protein signal transduction pathway activating substance in the medium is reduced (e.g., using a medium containing BMP4 at a concentration of 0.5 nM to 1.5 nM). The optimum concentration can be set through preliminary experiments.

On the other hand, in the first embodiment, the "low concentration" when SAG is used as the substance acting on the Shh signaling pathway is, for example, 0.1 μM to 2.0 μM, preferably 0.2 μM to 1.5 μM, more preferably 0.3 μM to 1.0 μM. The concentration of the substance acting on the Shh signaling pathway may not be constant over the entire period of the step (1). For example, the substance acting on the Shh signaling pathway may not be added to the medium for 3 to 8 days (6 days as a specific example) from the beginning of the suspension culture and then added thereto. The optimum concentration can be set through preliminary experiments.

In another embodiment (hereinafter referred to as "second embodiment"), the differentiation into the ventral hypothalamus is induced. In this embodiment, the "low concentration" when BMP4 is used as the bone morphogenetic protein signal transduction pathway activating substance is, for example, 0.1 nM to 3.0 nM, preferably 0.3 nM to 2.0 nM, more preferably 0.5 nM to 1.5 nM. The concentration of the bone morphogenetic protein signal transduction pathway activating substance may not be constant over the entire period of the step (1). For example, the bone morphogenetic protein signal transduction pathway activating substance may not be added to the medium for 3 to 8 days (6 days as a specific example) from the beginning of the suspension culture, and then added thereto. In addition, the concentration of the bone morphogenetic protein signal transduction pathway activating substance may be reduced during the culture. For example, the bone morphogenetic protein signal transduction pathway activating substance is not added to the medium for 3 to 8 days (6 days as a specific example) from the beginning of the suspension culture, and the culture is performed under the condition where the concentration of the bone morphogenetic protein signal transduction pathway activating substance in the medium is relatively high (for example, using a medium containing BMP4 at a concentration of 0.5 nM to 1.5 nM) for the subsequent 6 to 12 days (9 days as a specific example). For the subsequent 1 to 5 days (3 days as a specific example), the culture was performed under the condition where the concentration of the bone morphogenetic protein signal transduction pathway activating substance in the medium is reduced (e.g., using a medium containing BMP4 at a concentration of 0.25 nM to 0.75 nM). The optimum concentration can be set through preliminary experiments.

On the other hand, in the second embodiment, the "low concentration" when SAG is used as the substance acting on the Shh signaling pathway is, for example, 0.1 µM to 2.0 µM, preferably 0.2 µM to 1.5 µM, more preferably 0.3 µM to 1.0 µM. The concentration of the substance acting on the Shh signaling pathway may not be constant over the entire period of the step (1). For example, the substance acting on the Shh signaling pathway may not be added to the medium for 3 to 8 days (6 days as a specific example) from the beginning of the suspension culture and then added thereto. The optimum concentration can be set through preliminary experiments.

Those skilled in the art can set the concentration to be adopted when using the bone morphogenetic protein signal transduction pathway activating substance other than BMP4, i.e., the range of the "low concentration," according to the above concentration range, considering the difference in properties (especially the difference in activity) between the substance to be used and BMP4. Whether or not the set concentration range is appropriate can be confirmed by preliminary experiments according to the Examples which will be described later. The same is true for the use of a substance acting on the Shh signaling pathways other than SAG. Thus, the "low concentration" for the bone morphogenetic protein signal transduction pathway activating substance and the substance acting on the Shh signaling pathway can be recognized and understood by those skilled in the art without any particular difficulty.

The medium used in the second embodiment preferably contains an Akt inhibitor in addition to a low concentration of the bone morphogenetic protein signal transduction pathway activating substance and a low concentration of the substance acting on the Shh signaling pathway. The Akt inhibitor acts as a ventralization signal and promotes efficient differentiation into the ventral hypothalamus. As the Akt inhibitor, Akt inhibitor VIII (1,3-Dihydro-1-(1-((4-(6-phenyl-1H-imidazo[4,5-g]quinoxalin-7-yl)phenyl)methyl) 4-piperidin yl)-2H-benzimidazol-2-one, for example, provided by Calbiochem) can be used. The concentration of the Akt inhibitor can also be varied depending on the Akt inhibitor to be used. For example, when Akt inhibitor VIII is used, the concentration is, for example, 0.1 µM to 2.0 µM, preferably 0.2 µM to 1.5 µM, more preferably 0.3 µM to 1.0 µM. The optimum concentration can be set through preliminary experiments.

In order to suppress cell death of human pluripotent stem cells induced by dissociation, it is preferable to add an inhibitor of Rho-associated coiled-coil kinase (ROCK) to a medium to be used in the step (1) from the beginning of the culture (see JP 2008-99662 A). The ROCK inhibitor is added, for example, within 15 days, preferably within 10 days, more preferably within 6 days from the beginning of the culture. Examples of the ROCK inhibitor include Y-27632 ((+)-(R)-trans-4-(1-aminoethyl)-N-(4-pyridyl)cyclohexanecarboxamide dihydrochloride) and the like. The ROCK inhibitor is used at a concentration enough to suppress cell death of the human pluripotent stem cells induced by dissociation. For example, when Y-27632 is used, the concentration is, for example, about 0.1 to 200 µM, preferably about 2 to 50 µM. The concentration of the ROCK inhibitor may be varied within the addition period, and, for example, can be halved in the latter half of the addition period. The optimum concentration can be set through preliminary experiments.

As the medium to be used for suspension culture, a medium used for culturing mammalian cells can be prepared as a basal medium. Examples of the basal medium include, but not limited to, BME medium, BGJb medium, CMRL 1066 medium, Glasgow MEM medium, Improved MEM Zinc Option medium, IMDM medium, Medium 199 medium, Eagle MEM medium, αMEM medium, DMEM medium, ham medium, Ham's F-12 Such as a medium, RPMI 1640 medium, Fischer's medium, Neurobasal medium, and a mixed medium thereof, as long as it is a medium that can be used for culturing mammalian cells. In one embodiment, a mixed medium of IMDM medium and Ham's F-12 medium is used. The mixing ratio is, for example, IMDM: Ham's F-12=0.8 to 1.2:1.2 to 0.8 in a volume ratio.

Either a serum-containing medium or a serum-free medium can be used. In order to avoid contamination with unknown or unintended components, it is preferable to use a serum-free medium.

The medium used in the suspension culture may contain a serum alternative. The serum alternative may contain, for example, albumin, transferrin, a fatty acid, a collagen precursor, a trace element, 2-mercaptoethanol or 3' thiol glycerol, or an equivalent thereof. Serum alternatives can be prepared by known methods (see for example WO 98/30679). Commercially available serum alternatives can also be used. Examples of the commercially available serum alternatives include KSR (manufactured by Invitrogen), Chemically-defined Lipid concentrated (manufactured by Gibco), and Glutamax (manufactured by Gibco).

The medium used for culturing the cell aggregate in suspension can contain other additives on the condition that the induction of differentiation of human pluripotent stem cells into the target tissue is not adversely affected. Examples of the additives include insulin, an iron source (e.g., transferrin), a mineral (e.g., sodium selenate), a saccharide (e.g., glucose), an organic acid (e.g., pyruvic acid or lactic acid), a serum protein (e.g., albumin), an amino acid (e.g., L-glutamine), a reducing agent (e.g., 2-mercaptoethanol), a vitamin (e.g., ascorbic acid or d-biotin), an antibiotic (e.g., streptomycin, penicillin or gentamicin), and a buffer (e.g., HEPES).

In one embodiment, from the viewpoint that the medium used for suspension culture does not adversely affect the induction of differentiation into the target tissue, the medium is a chemically synthesized medium free from a growth factor other than those clearly described in the present specification as being included in the medium therein (growth-factor-free Chemically Defined Medium; gfCDM) to which a serum alternative (for example, KSR) is added. The "growth factor" used herein includes pattern formation factors such as Fgf; BMP; Wnt, Nodal, Notch, Shh and the like; insulin and Lipid-rich albumin. As the chemically synthesized medium free of a growth factor, for example, gfCDM disclosed in Wataya et al., Proc Natl Acad Sci USA, 105 (33): 11796-11801, 2008 can be indicated.

Figure 5:
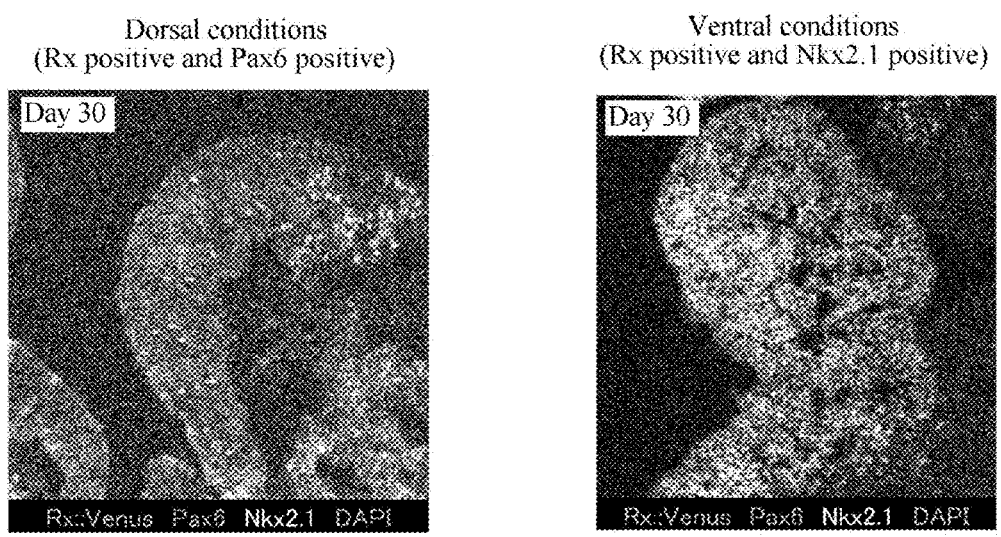
FIG. 5 shows a cell structure (left) on Day 30 of culture under dorsal hypothalamic induction conditions and cellular structure (right) on Day 30 of culture under ventral hypothalamus induction conditions. Rx: Venus: Green, Pax6: Red, Nkx2.1: White, DAPI: Blue.

In the step (1), initial orientation for the differentiation from undifferentiated cells to hypothalamus is carried out. As a result of the initial orientation of the step (1), the differentiation into the dorsal or ventral hypothalamus is ensured during the course of the next step (2). For example, when the differentiation into the dorsal hypothalamus is induced in the step (2), characteristics (Pax6 expression or the like) unique to the dorsal hypothalamus will be typically exhibited around 30 days after the beginning of the culture (see FIG. 5).

Aggregates of cells that can become hypothalamus in the future, i.e., aggregates of hypothalamic precursor cells can be obtained by performing the culture in the step (1). The step (1) may be carried out, for example, until 10% or more, preferably 30% or more, more preferably 50% or more of the cell aggregates in culture contain hypothalamic precursor cells. The hypothalamic precursor cells can be detected, for example, by RT-PCR or immunohistochemistry using a hypothalamic precursor cell marker-specific antibody. Rx is preferably used as a hypothalamic precursor cell marker. The culture period may vary depending on the types of the bone morphogenetic protein signal transduction pathway activating substance and substance acting on the Shh signaling pathway to be used, but, for example, the culture period is 10 to 26 days (18 days as a specific example).

In a preferred embodiment, a qualitatively uniform population of human pluripotent stem cell aggregates is cultured in suspension in a medium containing a low concentration of the bone morphogenetic protein signal transduction pathway activating substance and a low concentration of the substance acting on the Shh signaling pathway. The use of a qualitatively uniform population of human pluripotent stem cell aggregates can minimize differences in levels of differentiation among the cell aggregates and improve the differentiation induction efficiency. The following embodiments (A) and (B) can be indicated as examples of the suspension culture of a qualitatively uniform population of aggregates of pluripotent stem cells.

(A) Plural culture compartments are prepared, and a qualitatively uniform population of human pluripotent stem cell aggregates is seeded so that one culture compartment contains one human pluripotent stem cell aggregate. (For example, one human pluripotent stem cell aggregate is placed in each well of a 96-well plate.) Then, in each of the culture compartments, one human pluripotent stem cell aggregate is cultured in suspension in a medium containing a low concentration of a bone morphogenetic protein signal transduction pathway activating substance and a low concentration of a substance acting on the Shh signaling pathway.

(B) A qualitatively uniform population of human pluripotent stem cell aggregates is seeded in one culture compartment so that one culture compartment contains plural human pluripotent stem cell aggregates. (For example, plural human pluripotent stem cell aggregates are placed in a 10-cm dish.) Then, in the compartment, the plural human pluripotent stem cell aggregates are cultured in suspension in a medium containing a low concentration of a bone morphogenetic protein signal transduction pathway activating substance and a low concentration of a substance acting on the Shh signaling pathway.

In the method of the present invention, either the embodiment (A) or (B) can be adopted. Further, the embodiment may be changed during the culture in the method according to the present invention (change from the embodiment (A) to the embodiment (B) or from the embodiment (B) to the embodiment (A)). In one embodiment, the embodiment (A) is adopted for the culture in the step (1) and the embodiment (B) is adopted in the culture in the step (2).

Step (2)

In step (2) subsequent to the step (1), the cell aggregate obtained in the step (1) is further cultured in suspension in a medium containing a low concentration of a substance acting on the Shh signaling pathway. This step induces further differentiation into hypothalamic tissue. The culture conditions which are not specifically mentioned (culture method (preferably static culture is adopted), possibility of using feeder cells (preferably, culture is performed in the absence of feeder cells), usable culture vessel, basal medium to be used, additives other than the substance acting on the Shh signaling pathway, etc.) are similar to those in the step (1). Hereinafter, the culture conditions characteristic of the step (2) will be described.

The step (2) is preferably carried out under a high oxygen partial pressure condition. By suspension culture under a high oxygen partial pressure condition, the arrival of oxygen at the inside of the cell aggregate and the long-term maintenance culture of the cell aggregate are achieved, thereby enabling efficient differentiation induction into hypothalamic tissue.

The "high oxygen partial pressure condition" means an oxygen partial pressure condition exceeding the oxygen partial pressure (20%) in the air. The oxygen partial pressure in the step (2) is, for example, 30 to 60%, preferably 35 to 60%, more preferably 38 to 60% (40% as a specific example).

The other culture conditions such as the culture temperature and $CO_2$ concentration in the suspension culture in the step (2) can be set appropriately. The culture temperature is, for example, about 30 to 40° C., preferably about 37° C. The $CO_2$ concentration is, for example, about 1 to 10%, preferably about 5%.

The medium used in the step (2) contains a substance acting on the Shh signaling pathway at a low concentration. In the first embodiment (the embodiment in which the differentiation into dorsal hypothalamic tissue is induced), the "low concentration" when SAG is used as the substance acting on the Shh signaling pathway means, for example, 0.1 μM to 2.0 μM, preferably 0.2 μM to 1.5 μM, more preferably 0.3 μM to 1.0 μM. A similar concentration is adopted also in the second embodiment (the embodiment in which the differentiation into ventral hypothalamic tissue is induced). The concentration of the substance acting on the Shh signaling pathway may not be constant over the entire period of the step (2) as long as the effect (i.e., differentiation induction into dorsal hypothalamic tissue or ventral hypothalamic tissue) necessary for the present invention is obtained. The optimum concentration can be set through preliminary experiments.

Those skilled in the art can set the concentration to be adopted when a substance acting on the Shh signaling pathway other than SAG is used, i.e., the range of the "low concentration" according to the above concentration range, considering the difference in properties (especially the difference in activity) between the substance to be used and SAG. Whether or not the set concentration range is appropriate can be confirmed by preliminary experiments according to the Examples which will be described later. Thus, also in the step (2), the "low concentration" for the substance acting on the Shh signaling pathway can be recognized and understood by those skilled in the art without any particular difficulty.

The medium used in the step (2) preferably does not contain a bone morphogenetic protein signal transduction pathway activating substance. In other words, in the step (2), it is preferable to use a medium that contains a substance acting on the Shh signaling pathway at a low concentration, but does not contain a bone morphogenetic protein signal transduction pathway activating substance. According to this condition, the effects of avoiding cyst formation of the cell aggregates due to long-term exposure of the bone morphogenetic protein signal transduction pathway activating substance and the change in direction of differentiation (change in direction of differentiation from hypothalamus into a neural retina) can be obtained.

The medium used in the step (2) of the second embodiment preferably contains an Akt inhibitor in addition to a low concentration of the substance acting on the Shh signaling pathway. The Akt inhibitor acts as a ventralization signal and promotes efficient differentiation into the ventral hypothalamus. Preferable Akt inhibitors and the use concentrations thereof are similar to those exemplified in the second embodiment of the step (1) described above.

The culture in the step (2) is performed for a period of time sufficient to further induce differentiation into hypothalamic tissue (dorsal hypothalamus or ventral hypothalamus). The fact that further induction into hypothalamic tissue has occurred can be confirmed by detection of a hypothalamic tissue-specific marker. Pax6 and/or Nkx2.1 are/is preferably used as marker(s) of hypothalamic tissue. Rx is preferably used together. Typically, the dorsal hypothalamic tissue is an Rx positive, Pax6 positive and Nkx2.1 negative tissue, and the ventral hypothalamic tissue is an Rx positive, Pax6 negative and Nkx2.1 positive tissue.

The progress of the differentiation into dorsal hypothalamic tissue (in the case of the first embodiment) can be confirmed based on the appearance of neural precursor cells characteristic of dorsal hypothalamic tissue (e.g., vasopressin (AVP) neuron precursor cells, oxytocin (OXT) neuron precursor cells, thyrotropin releasing hormone (TRH) neuron precursor cells, corticotropin releasing hormone (CRH) neuron precursor cells, and neuropeptide Y (NPY) neuron precursor cells). When neural precursor cells characteristic of dorsal hypothalamic tissue are observed, it can be determined that the induction of differentiation into dorsal hypothalamic tissue has been further advanced. For confirmation of the appearance of neural precursor cells, markers characteristic of the respective neural precursor cells can be used. For example, if the expression of Otp and Brn2 is observed, it can be determined that AVP neuron precursor cells appear.

On the other hand, the occurrence of further induction into ventral hypothalamic tissue (in the second embodiment) can be confirmed based on the appearance of neural precursor cells characteristic of ventral hypothalamic tissue (e.g., agouti related protein (AgRP) neuron precursor cells, proopiomelanocortin (POMC) neuron precursor cells, melanin concentrating hormone (MCH) neuron precursor cells, and Orexin neuron precursor cells). When neural precursor cells characteristic of dorsal hypothalamic tissue are observed, it can be determined that the induction of differentiation into dorsal hypothalamic tissue has been further advanced. For confirmation of the appearance of neural precursor cells, markers characteristic of the respective nerve cells can be used.

The culturing period of the step (2) can vary depending on the type of the substance acting on the Shh signaling pathway to be used, and is, for example, 20 to 100 days, preferably 30 to 80 days (30 days, 40 days, 50 days, 60 days, 70 days, and 80 days, as specific examples).

Step (3)

In the producing method of the present invention, preferably, the following step (3) is performed in addition to the steps (1) and (2):

(3) recovering the cell aggregate obtained in the step (2) and subjecting the cells constituting the cell aggregate to dissociation culture.

By the step (3), the induction of differentiation into hypothalamic tissue is further promoted, and maturation occurs. In other words, the step (3) provides further improvement in differentiation efficiency. The culture in the step (3) corresponds to a dissociation culture which is considered to be advantageous in culture of nerve cells. By the step (3), culture is switched from the three-dimensional culture called suspension culture to two-dimensional culture.

In the dissociation culture, first, the cell aggregates are recovered to dissociate the cells (separated into single cells). For the dissociation of the cells, proteolytic enzymes such as EDTA-trypsin, collagenase IV and metalloprotease can be used alone or appropriately in combination. Cell dissociating solutions with low cell toxicity are preferred. As such cell dissociation solutions, commercially available products such as DISPASE (EIDIA Co., Ltd.), TrypLE (Invitrogen) or Accutase (MILLIPORE) are available.

The resultant single cells are seeded in a culture vessel suitable for dissociation culture. The culture vessel used in the dissociation culture is not particularly limited. For example, dishes, Petri dishes, tissue culture dishes, multi-dishes, microplates, microwell plates, multi-plates, multi-well plates, chamber slides, laboratory dishes, and the like can be used. In order to enhance the adhesion of the cells to the culture surface, it is preferable to use a culture vessel coated with matrigel (BD), poly-D-lysine, poly-L-lysine, collagen, gelatin, laminin, heparan sulfate proteoglycan, entactin or a combination of two or more thereof.

The step (3) is preferably carried out under a high oxygen partial pressure condition. Plane culture under a high oxygen partial pressure condition makes differentiation into nerve cells easier.

The "high oxygen partial pressure condition" means an oxygen partial pressure condition exceeding the oxygen partial pressure (20%) in the air. The oxygen partial pressure in the step (3) is, for example, 30 to 60%, preferably 35 to 60%, more preferably 38 to 60% (40% as a specific example).

The other culture conditions such as the culture temperature, $CO_2$ concentration, and $O_2$ concentration in the dissociation culture can be set appropriately. The culture temperature is, for example, about 30 to 40° C., preferably about 37° C. The $CO_2$ concentration is, for example, about 1 to 10%, preferably about 5%. The $O_2$ concentration is, for example, about 20%.

As a medium used in the dissociation culture, a medium used for culturing mammalian cells can be prepared as a basal medium. Examples of the basal medium include, but not limited to, BME medium, BGJb medium, CMRL 1066 medium, Glasgow MEM medium, Improved MEM Zinc Option medium, IMDM medium, Medium 199 medium, Eagle MEM medium, αMEM medium, DMEM medium, ham medium, Ham's F-12 Such as a medium, RPMI 1640 medium, Fischer's medium, Neurobasal medium, and a mixed medium thereof, as long as it is a medium that can be used for culturing mammalian cells. In one embodiment, a mixed medium of DMEM medium and Ham's F-12 medium (e.g., DMEM/F-12 Catalog No. D6421 from Sigma Aldrich) is used.

Either a serum-containing medium or a serum-free medium can be used. In order to avoid contamination with unknown or unintended components, it is preferable to use a serum-free medium.

Preferably, a medium having a ciliary neurotrophic factor (CNTF), a brain-derived neurotrophic factor (BDNF), a neurotrophin 3 (NT-3), a fetal bovine serum, an N2 supplement, a B27 supplement, or the like added is used to promote the proliferation and differentiation of nerve cells. In a preferred embodiment, a medium having the N2 supplement and the B27 supplement added is used. The content of the N2 supplement in the medium is, for example, 1% of the total amount in a volume ratio. Similarly, the content of the B27 supplement in the medium is, for example, 2% of the total amount in a volume ratio. Incidentally, the N2 supplement is available from Gibco (product name N2 supplement (×100)) etc., and the B27 supplement is available from Gibco (product name B27 supplement (×100)) etc. BDNF can also be substituted with LM22A-4(N1,N3,N5-Tris(2-hydroxyethyl)-1,3,5-benzenetricarboxamide (available from SIGMA-ALDRICH) which is a BDNF agonist).

The medium used in the dissociation culture may contain a serum alternative and/or other additives. Examples of the other additives include insulin, an iron source (e.g., transferrin), a mineral (e.g., sodium selenate), a saccharide (e.g., glucose), an organic acid (e.g., pyruvic acid or lactic acid), a serum protein (e.g., albumin), an amino acid (e.g., L-glutamine), a reducing agent (e.g., 2-mercaptoethanol), a vitamin (e.g., ascorbic acid or d-biotin), an antibiotic (e.g., streptomycin, penicillin or gentamicin), and a buffer (e.g., HEPES).

There are various reports on dissociation culture of nerve cells (for example, Wataya T. et al., Proc Natl Acad Sci USA 105 (33): 11796-11801 (2008)), and the conditions to be adopted in the dissociation culture of the present invention can be set or adjusted with reference to those reports.

The culture in the step (3) is performed for a period sufficient for differentiation and maturation of hypothalamic nerve cells. In the case of the first embodiment (embodiment in which the differentiation into dorsal hypothalamic tissue is induced), the occurrence of sufficient differentiation and maturation of hypothalamic nerve cells can be confirmed based on the presence or absence and presence ratio of a nerve cell observed to be localized in the dorsal hypothalamic tissue (e.g., AVP neuron, OXT neuron, TRH neuron, CRH neuron, or NPY neuron) and/or the presence or absence and amount of a hormone produced by the nerve cell. For example, if the production of AVP is observed, functional AVP neurons have appeared and it can be determined that sufficient differentiation/maturation of nerve cells has occurred. Also with respect to other nerve cells observed to be localized in the dorsal hypothalamic tissue, the presence or absence or extent of the differentiation/maturation thereof can be determined based on the hormone produced by each of the nerve cells as an index.

Similarly, in the case of the second embodiment (embodiment in which the differentiation into ventral hypothalamic tissue is induced), the occurrence of sufficient differentiation/maturation of nerve cells can be confirmed based on the presence or absence and presence ratio of a nerve cell observed to be localized in the ventral hypothalamic tissue (e.g., AgRP neuron, POMC neuron, MCH neuron, or Orexin neuron) and/or the presence or absence and amount of a hormone produced by the nerve cell.

The culturing period of the step (3) may vary depending on the culture conditions, and is, for example, 30 to 150 days, preferably 40 to 110 days (40 days, 50 days, 60 days, 70 days, 80 days, 90 days, 100 days, and 110 days as specific examples).

2. Method for Producing Cellular Structure Including Hypothalamic Tissue and Pituitary Tissue A second aspect of the present invention relates to a method for producing a cellular structure comprising hypothalamic tissue and pituitary tissue (hereinafter also referred to as "hybrid cellular structure"). In the producing method of the present invention, the following steps (i) to (iii) are carried out. Incidentally, the matters which are not specifically mentioned are similar to those in the first aspect, and the corresponding explanations are applied thereto.

The steps are:
(i) culturing an aggregate of human pluripotent stem cells in suspension in a medium containing a bone morphogenetic protein signal transduction pathway activating substance and a substance acting on the Shh signaling pathway,
(ii) further culturing the cell aggregate formed in the step (i) in suspension in a medium containing a bone morphogenetic protein signal transduction pathway activating substance and a substance acting on the Shh signaling pathway, and
(iii) culturing the cell aggregate obtained in the step (ii) in suspension in a medium suitable for simultaneous induction of pituitary and hypothalamus.

Step (i)

In step (i), first, a human pluripotent stem cell aggregate is prepared by a means similar to that in the first aspect of the present invention, and cultured in suspension in a medium containing a bone morphogenetic protein signal transduction pathway activating substance and a substance acting on the Shh signaling pathway.

The suspension culture of the cell aggregates may be performed under either condition, i.e., in the presence/absence of feeder cells, but is preferably performed in the absence of feeder cells from the viewpoint of avoiding contamination of undetermined factors.

The other culture conditions such as the culture temperature, $CO_2$ concentration, and $O_2$ concentration in the suspension culture of the cell aggregates can be set appropriately. The culture temperature is, for example, about 30 to 40° C., preferably about 37° C. The $CO_2$ concentration is, for example, about 1 to 10%, preferably about 5%. The $O_2$ concentration is, for example, about 20%.

BMP2, BMP4, BMP7, GDF5, and the like can be used as the bone morphogenetic protein signal transduction pathway activating substance. Preferably, BMP4 is used as the bone morphogenetic protein signal transduction pathway activating substance. On the other hand, as the substance capable of acting on the Shh signaling pathway, proteins belonging to the Hedgehog family (e.g., Shh), Shh receptors, Shh receptor agonists, Purmorphamine, Smoothened Agonist (SAG) (3-Chloro-N-[trans-4-methylamino)cyclohexyl]-N-[[3-(4-pyridinyl)phenyl]methyl]-benzo[b]thiophene-2-carboxamide. Preferably, SAG is used. A preferable combination of a bone morphogenetic protein signal transduction pathway activating substance and substance acting on the Shh signaling pathway is a combination of BMP4 and SAG.

The concentration of the bone morphogenetic protein signal transduction pathway activating substance in the medium can be appropriately set within a range that can induce differentiation into hypothalamus and pituitary, but, when BMP4 is used as the bone morphogenetic protein signal transduction pathway activating substance, the concentration thereof is, for example, 0.01 to 1000 nM, preferably 0.1 to 100 nM, more preferably 1 to 10 nM (5 nM as a specific example). The concentration of the bone morphogenetic protein signal transduction pathway activating substance may not be constant over all periods of the step (i). For example, the bone morphogenetic protein signal transduction pathway activating substance may not be added to the medium for 3 to 8 days (6 days as a specific example) from the beginning of the suspension culture, and then added thereto. The optimum concentration can be set through preliminary experiments.

The concentration of the substance acting on the Shh signaling pathway in the medium can be appropriately set within a range where the differentiation into hypothalamus and pituitary can be induced, but, when SAG is used as the substance acting on the Shh signaling pathway, the concentration thereof is, for example, 1 nM to 1000 μM, preferably 10 nM to 100 μM, more preferably 100 nM to 10 μM (2 μM as a specific example). The concentration of the substance acting on the Shh signaling pathway may not be constant over the entire period of the step (i). For example, the substance acting on the Shh signaling pathway may not be added to the medium for 3 to 8 days (6 days as a specific example) from the beginning of the suspension culture and then added thereto. The optimum concentration can be set through preliminary experiments.

In order to suppress cell death of the human pluripotent stem cells induced by dissociation, it is preferable to add a Rho-associated coiled-coil kinase (ROCK) inhibitor to the medium used in the step (i) from the beginning of the culture (see JP 2008-99662 A). The ROCK inhibitor is added, for example, within 15 days, preferably within 10 days, more preferably within 6 days from the beginning of the culture. Examples of the ROCK inhibitor include Y-27632 ((+)-(R)-trans-4-(1-aminoethyl)-N-(4-pyridyl)cyclohexanecarboxamide dihydrochloride) and the like. The ROCK inhibitor is used at a concentration enough to suppress cell death of the human pluripotent stem cells induced by dissociation. For example, when Y-27632 is used, the concentration is, for example, about 0.1 to 200 μM, preferably about 2 to 50 μM. The concentration of the ROCK inhibitor may be varied within the addition period, and, for example, can be halved in the latter half of the addition period. The optimum concentration can be set through preliminary experiments.

The matters which are not specifically mentioned, such as usable basal medium and substances that can be contained in the medium, are similar to those in the step (1) of the first aspect.

The culture in the step (i) is performed for a period of time sufficient to induce differentiation of human pluripotent stem cells into hypothalamic neuroepithelial tissue and surface ectoderm. The differentiation into hypothalamic neuroepithelial tissue and surface ectoderm can be detected by, for example, RT-PCR or immunohistochemistry using an antibody specific to a marker of hypothalamic neuroepithelial tissue and surface ectoderm. For example, the culture is performed until 10% or more, preferably 30% or more, more preferably 50% or more of cell aggregates in the culture contains hypothalamic neuroepithelial tissue and surface ectoderm. The culture period may vary depending on the types of the bone morphogenetic protein signal transduction pathway activating substance and substance acting on the Shh signaling pathway to be used, but, for example, the culture period is 15 to 20 days (18 days as a specific example).

The "hypothalamic neuroepithelial tissue" refers to a neuroepithelial tissue expressing a hypothalamic marker. Examples of the hypothalamic marker include NKx2.1 (ventral hypothalamic marker) and Pax6 (dorsal hypothalamic marker). In one embodiment, ventral hypothalamic neuroepithelial tissue is an Rx-positive, Chx10-negative, and Nkx2.1-positive neuroepithelial tissue. In one embodiment, dorsal hypothalamic neuroepithelial tissue is an Rx-positive, Chx10-negative, and Pax6-positive neuroepithelial tissue.

The "surface ectoderm" is an ectodermal cell layer formed on the surface layer of an embryo in embryonic development. As the surface ectoderm marker, pan-cytokeratin is indicated. The surface ectoderm can be generally differentiated into anterior pituitary, skin, oral cavity epithelium, dental enamel, dermal gland, and the like. In one embodiment, surface ectoderm is a cell layer that is E-cadherin positive and pan-cytokeratin positive.

Suitably, in the cell aggregate obtained in the step (i), hypothalamic neuroepithelial tissue occupies the inside of the cell aggregate, and the cells of a single layer surface ectoderm constitutes the surface of the cell aggregate. The surface ectoderm may contain thickened epidermal placode in a part thereof.

In one preferred embodiment, a qualitatively uniform population of human pluripotent stem cell aggregates is cultured in suspension in a medium containing a bone morphogenetic protein signal transduction pathway activating substance and a substance acting on the Shh signaling pathway. The use of a qualitatively uniform population of human pluripotent stem cell aggregates can minimize differences in levels of differentiation among the cell aggregates and improve the differentiation induction efficiency. The following embodiments (A) and (B) can be indicated as examples of the suspension culture of a qualitatively uniform population of aggregates of pluripotent stem cells.

(A) Plural culture compartments are prepared, and a qualitatively uniform population of human pluripotent stem cell aggregates is seeded so that one culture compartment contains one human pluripotent stem cell aggregate. (For example, one human pluripotent stem cell aggregate is placed in each well of a 96-well plate.) Then, in each of the culture compartments, one human pluripotent stem cell aggregate is cultured in suspension in a medium containing a bone morphogenetic protein signal transduction pathway activating substance and a substance acting on the Shh signaling pathway.

(B) A qualitatively uniform population of human pluripotent stem cell aggregates is seeded in one culture compartment so that one culture compartment contains plural human pluripotent stem cell aggregates. (For example, plural human pluripotent stem cell aggregates are placed in a 10-cm dish.) Then, in the compartment, the plural human pluripotent stem cell aggregates are cultured in suspension in a medium containing a bone morphogenetic protein signal transduction pathway activating substance and a substance acting on the Shh signaling pathway.

In the method of the present invention, either the embodiment (A) or (B) can be adopted. Further, the embodiment may be changed during the culture in the method according to the present invention (change from the embodiment (A) to the embodiment (B) or from the embodiment (B) to the embodiment (A)). In one embodiment, the embodiment (A) is adopted for the culture in the step (i) and the embodiment (B) is adopted for the culture in the step (ii).

Step (ii)

In step (ii) following the step (i), the cell aggregate obtained in the step (i) is further cultured in suspension in a medium containing a bone morphogenetic protein signal transduction pathway activating substance and a substance acting on the Shh signaling pathway. This step induces further differentiation into hypothalamus and pituitary. The culture conditions which are not specifically mentioned (culture method (preferably static culture is adopted), possibility of using feeder cells (preferably culture is performed in the absence of feeder cells), usable culture vessel, basal medium to be used, additives other than bone morphogenetic protein signal transduction pathway activating substance and a substance acting on the Shh signaling pathway, etc.) are similar to those in the step (i). Hereinafter, the culture conditions characteristic of the step (ii) will be described.

The step (ii) is preferably carried out under a high oxygen partial pressure condition. By suspension culture under a high oxygen partial pressure condition, the arrival of oxygen at the inside of the cell aggregate and the long-term maintenance culture of the cell aggregate are achieved, thereby enabling efficient differentiation induction into hypothalamic tissue and pituitary tissue.

The "high oxygen partial pressure condition" means an oxygen partial pressure condition exceeding the oxygen partial pressure (20%) in the air. The oxygen partial pressure in the step (ii) is, for example, 30 to 60%, preferably 35 to 60%, more preferably 38 to 60% (40% as a specific example).

The other culture conditions such as the culture temperature and $CO_2$ concentration in the suspension culture in the step (ii) can be set appropriately. The culture temperature is, for example, about 30 to 40° C., preferably about 37° C. The $CO_2$ concentration is, for example, about 1 to 10%, preferably about 5%.

The medium to be used in the step (ii) contains a bone morphogenetic protein signal transduction pathway activating substance and a substance acting on the Shh signaling pathway. The concentration of the bone morphogenetic protein signal transduction pathway activating substance in the medium can be appropriately set within a range that can induce differentiation into hypothalamus and pituitary, but, when BMP4 is used as the bone morphogenetic protein signal transduction pathway activating substance, the concentration thereof is, for example, 0.01 to 1000 nM, preferably 0.1 to 100 nM, more preferably 1 to 10 nM (5 nM as a specific example). The concentration of the bone morphogenetic protein signal transduction pathway activating substance may be decreased during the culture. For example, the above-mentioned concentration is used at the start of the step (ii), and the concentration can be reduced stepwise so that the concentration is halved every 2 to 4 days. The optimum concentration can be set through preliminary experiments.

The concentration of the substance acting on the Shh signaling pathway in the medium can be appropriately set within a range where the differentiation into hypothalamus and pituitary can be induced, but, when SAG is used as the substance acting on the Shh signaling pathway, the concentration thereof is, for example, 1 nM to 1000 μM, preferably 10 nM to 100 μM, more preferably 100 nM to 10 μM (2 μM as a specific example). The optimum concentration can be set through preliminary experiments.

In one embodiment, the medium to be used in the step (ii) contains FGF2. FGF2 promotes differentiation of surface ectoderm into pituitary placode. The concentration of FGF2 in the medium is usually 1 to 1000 ng/ml, preferably 10 to 100 ng/ml. The optimum concentration can be set through preliminary experiments.

FGF2 is a known cytokine also called basic fibroblast growth factor (bFGF), and the amino acid sequence thereof is also known. FGF2 to be used in the present invention is usually mammalian FGF2. Examples of the mammals include experiment animals such as rodents such as mice, rats, hamsters and guinea pigs, and the like, rabbits and the like; domestic animals such as swines, bovines, goats, horses and sheep; companion animals such as dogs and cats; and primates such as humans, monkeys, orangutans and chimpanzees. Since FGF2 has cross-reactivity among many mammalian species, FGF2 of any mammal may be used as long as the object of the present invention can be achieved, but FGF2 is preferably FGF2 of rodents (for example, mouse or rat) or primates (for example, human), most preferably human FGF2. The "human FGF2" means FGF2 having an amino acid sequence of FGF2 naturally expressed in the human body. As a representative amino acid sequence of human FGF2, NCBI accession number, NP-001997.5 (updated on Feb. 18, 2014) can be exemplified.

The culturing period of the step (ii) may vary depending on the types of the bone morphogenetic protein signal transduction pathway activating substance and the substance acting on the Shh signaling pathway to be used, but for example, the culture period is 6 to 20 days, preferably 10 to 14 days (12 days as a specific example).

Step (iii)

The cell aggregate obtained in the step (ii) is subjected to further suspension culture. For the culture in this step, a medium suitable for simultaneous induction of pituitary and hypothalamus is used. In other words, the medium composition is changed to promote simultaneous induction of pituitary and hypothalamus.

In the culture in the step (iii), a medium containing a substance acting on the Shh signaling pathway is preferably used. The concentration of the substance acting on the Shh signaling pathway in the medium can be appropriately set within a range where the differentiation into hypothalamus and pituitary can be induced, but, when SAG is used as the substance acting on the Shh signaling pathway, the concentration thereof is, for example, 1 nM to 1000 μM, preferably 10 nM to 100 μM, more preferably 100 nM to 10 μM (2 μM as a specific example). On the other hand, it is preferable to use a medium containing components of the medium used in the dissociation culture in the above step (3) (preferably containing components that promote proliferation and differentiation of nerve cells). For example, a medium obtained by mixing the medium used in the dissociation culture in the above step (3) and the medium used in the culture in the above step (ii) in a volume ratio of 1:1 is used. In addition, it is advisable to add a serum alternative (e.g., KSR) to the mixed medium in about 20% by volume. The optimum concentration can be set through preliminary experiments.

The culture in the step (iii) is performed for a period sufficient for hypothalamic maturation (differentiation/ maturation of hypothalamic nerve cells) and pituitary maturation. The occurrence of adequate maturation of hypothalamus can be confirmed based on the presence or absence and presence ratio of a nerve cell observed to be localized in the hypothalamic tissue (e.g., AVP neuron, OXT neuron, TRH neuron, CRH neuron, NPY neuron, AgRP neuron, POMC neuron, MCH neuron, or Orexin neuron) and/or the presence or absence and amount of a hormone produced by the nerve cell. On the other hand, the occurrence of adequate maturation of pituitary can be confirmed based on the presence or absence and presence ratio of pituitary hormone-producing cells (growth hormone (GH) producing cells, prolactin (PRL) producing cells, adrenocorticotropic hormone (ACTH) producing cells, thyroid stimulating hormone (TSH) producing cells, follicle-stimulating hormone (FSH) producing cells, luteinizing hormone producing cells, melanocyte stimulating hormone (MSH) producing cells, etc.) and/or the presence or absence and amount of a hormone produced by the cells.

The culturing period of the step (iii) may vary depending on the culture conditions, but is, for example, 50 days to 200 days, preferably 70 days to 150 days (70 days, 80 days, 90 days, 100 days, 110 days and 120 days, as specific examples).

In one embodiment, the following step (a) is performed between the steps (ii) and (iii):
(a) further culturing the cell aggregate obtained in the step (ii) in suspension in a medium containing a substance acting on the Shh signaling pathway.

In this embodiment, the cell aggregate obtained in the step (a) is subjected to the culture in the step (iii). Efficient differentiation into hypothalamus and pituitary is induced by the step (a). The culture conditions which are not specifically mentioned (culture method (preferably static culture is adopted), possibility of using feeder cells (preferably culture is performed in the absence of feeder cells), usable culture vessel, basal medium to be used, additives other than the substance acting on the Shh signaling pathway, etc.) are similar to those in the step (ii). Hereinafter, the culture conditions characteristic of the step (a) will be described.

In step (a), a medium containing a substance acting on the Shh signaling pathway is used. The concentration for the substance acting on the Shh signaling pathway in the medium can be appropriately set within a range where the differentiation into hypothalamus and pituitary can be induced, but, when SAG is used as the substance acting on the Shh signaling pathway, the concentration thereof is, for example, 1 nM to 1000 µM, preferably 10 nM to 100 µM, more preferably 100 nM to 10 µM (2 µM as a specific example). The optimum concentration can be set through preliminary experiments.

The medium used in the step (a) preferably does not contain a bone morphogenetic protein signal transduction pathway activating substance. In other words, in the step (a), it is preferable to use a medium that contains a substance acting on the Shh signaling pathway, but does not contain a bone morphogenetic protein signal transduction pathway activating substance. According to this condition, the effects of avoiding the cystification of the cell aggregates due to long-term exposure of the bone morphogenetic protein signal and the change in direction of differentiation can be obtained.

The medium used in the step (a) preferably contains a serum alternative. The concentration of the serum alternative in the medium can be appropriately set within the range where the differentiation into hypothalamus and pituitary can be induced, but when KSR is used as the serum alternative, the concentration thereof is, for example, 1% (v/v) to 30% (v/v), preferably 5% (v/v) to 20% (v/v) (10% (v/v) as a specific example).

The step (a) is preferably carried out under a high oxygen partial pressure condition. By suspension culture under a high oxygen partial pressure condition, the arrival of oxygen at the inside of the cell aggregate and the long-term maintenance culture of the cell aggregate are achieved, thereby enabling efficient differentiation induction into hypothalamic tissue and pituitary tissue.

The "high oxygen partial pressure condition" means an oxygen partial pressure condition exceeding the oxygen partial pressure (20%) in the air. The oxygen partial pressure in the step (a) is, for example, 30 to 60%, preferably 35 to 60%, more preferably 38 to 60% (40% as a specific example).

The culturing period of the step (a) may vary depending on the culture conditions, but is, for example, 10 days to 40 days, preferably 15 days to 30 days (20 days and 25 days as specific examples).

3. Uses of Cellular Structure and Cells Constituting the Cellular Structure

A cellular structure obtained by the producing method of the present invention, that is, a cellular structure including dorsal or ventral hypothalamic tissue or hybrid cellular structure, or a part thereof (tissue or cells constituting either of the cellular structures) is used, for example, for transplantation therapy. The "part of the cellular structure" can be prepared, for example, by cutting with a scalpel or the like, treatment with a proteolytic enzyme, EDTA, or the like. Prior to the application to transplantation therapy or the like, the prepared cells may be refined or purified using cell surface markers, morphology, secretory substances, etc. as indices.

In the transplantation therapy using a cellular structure comprising hypothalamic tissue or a part thereof, a disease caused by a hypothalamic disorder and a disease accompanied by a hypothalamic disorder (the above two diseases are referred to collectively as "hypothalamic disease" herein) are to be treated. On the other hand, in the transplantation therapy using a hybrid cellular structure or a part thereof, a disease caused by a hypothalamus and/or pituitary disorder and a disease accompanied by a hypothalamus and/or pituitary disorder (the above two diseases are referred to collectively as "hypothalamic/pituitary disease") are to be treated. The hybrid cellular structure is particularly suitable for treating pathological conditions in which both hypothalamus and pituitary are disordered since hypothalamic tissue and pituitary tissue, which are functionally inseparable, form a complex.

Examples of the diseases to which the cellular structure of the present invention or a part thereof can be applied include central diabetes insipidus, hypothalamic hypopituitarism, Prader's syndrome, Laurence-Moon-Biedl syndrome, hypothalamic obesity, eating disorders, cognitive dysfunction, sleep disorders, panhypopituitarism, pituitary dwarfism, hypoadrenocorticism, partial hypopituitarism, isolated deficiency of anterior pituitary hormone, and damage to hypothalamus and/or pituitary due to trauma, radiation therapy, resection or the like.

The transplantation site when the cellular structure of the present invention or a part thereof is used for transplantation therapy is not particularly limited as long as it exerts a function as hypothalamus and/or pituitary after transplantation, and examples thereof can include subrenal capsule, subcutaneous, peritoneum, cerebrum, hypothalamus and pituitary. As is apparent from the above description, the present application also provides a method for treating a hypothalamic disease or a hypothalamic pituitary disease, which includes transplanting the cellular structure of the present invention or cells constituting the cellular structure to a patient.

In transplantation therapy, rejection due to the difference in histocompatibility antigens often poses a problem, but the problem can be overcome by producing the cellular structure of the present invention using human pluripotent stem cells established from the somatic cells of a recipient. Therefore, in a preferred embodiment of the present invention, human pluripotent stem cells (e.g., iPS cells) established from the somatic cells of the recipient are used as the human pluripotent stem cells in the method of the present invention. According to this embodiment, a cellular structure constructed from autologous cells or a part thereof is transplanted into a recipient.

The cellular structure of the present invention or a part thereof can be used for drug screening and evaluation. Specifically, it can be applied to the screening of therapeutic agents for hypothalamic diseases or hypothalamic pituitary diseases, evaluation of the effectiveness of therapeutic drug candidates, toxicity tests, and the like. For example, iPS cells are prepared from a patient suffering from a hypothalamic disease or a hypothalamic pituitary disease, and a cellular structure is produced from the iPS cells by the producing method of the present invention. The obtained cellular structure or a part thereof is cultured in the presence of a test substance (test group). A control group is cultured in the absence of the test substance. Then, the degree of disorder is compared between the test group and the control group. The test substances which have an effect of alleviating the degree of disorder are selected as candidate substances for therapeutic agents. As the test substance, organic or inorganic compounds with any molecular size can be used. Examples of the organic compounds include nucleic acids, peptides, proteins, lipids (simple lipids, complex lipids (phosphoglycerides, sphingolipids, glycosylglycerides, cerebrosides, etc.), prostaglandins, isoprenoids, terpenes, steroids, polyphenols, catechins and vitamins (B1, B2, B3, B5, B6, B7, B9, B12, C, A, D, E, etc.). The test substance may be derived from natural products or obtained by synthesis. In the latter case, for example, an efficient screening system can be constructed by using a combinatorial synthesis technique. A plant extract, a cell extract, a culture supernatant, or the like may be used as the test substance. Also, an existing drug may be used as the test substance. By simultaneously adding two or more kinds of test substances, interactions, synergistic actions, and the like between the test substances may be examined.

EXAMPLES

A. Differentiation Induction from Human ES Cells
1. Study on Differentiation Induction Method from Human ES Cells into Hypothalamus
(1) Application of Previously Reported Method Wataya et al. established a method for inducing differentiation from mouse ES cells into hypothalamic neurons (Wataya T. et al., Proc Natl Acad Sci USA 105 (33): 11796-11801 (2008).). When mouse ES cells were used, the differentiation into AVP neurons was confirmed by this method (left in FIG. 1).

Next, it was examined whether the method can be applied also to human ES cells. Human ES cells (KhES-1) were subjected to maintenance culture by a conventional method on MEF and then used. To monitor differentiation induction into a hypothalamic tissue, KhES-1 wherein a Venus cDNA has been knocked-in into the gene of Rx which is a hypothalamic nerve marker was used. To differentiate human ES cells by Serum-Free Embryonic Body quick method (SFEBq method), human ES cells were dispersed to single cells using an enzyme by the method of Nakano et al. (Cell Stem Cell. 2012 Jun. 14; 10 (6): 771-85), and reaggregated using a low cell adhesive V-bottom 96-well plate (Sumitomo Bakelite Co., Ltd.). Ten thousand (10,000) cells were seeded per well and cultured in a gfCDM differentiation medium at 37° C. under 5% $CO_2$. With the day of seeding defined as Day 0 of differentiation culture, 20 μM Y-27632 (ROCK inhibitor: cell death suppressor at the time of dispersion: Watanabe et al. (Nat Biotechnol. 2007 June; 25 (6): 681-6. Epub 2007 May 27.)) was added from Day 0 to Day 3, and, on and after Day 3 of culture, a half of the medium was exchanged with a differentiation medium free from Y-27632 at a frequency of once every 3 days.

The results are shown on the right of FIG. 1. On Day 3 of culture, it was confirmed that no cell aggregate was formed. That is, although the SFEBq method was performed using the gfCDM medium, no formation of cell aggregate was observed.

(2) Study 1 on Components in Medium (Use of Serum Alternative)

Based on the thought that no aggregate was formed due to nutritional deficiency, a small amount of a serum alternative KSR was added to the gfCDM to verify the effect. Specifically, the SFEBq method was performed by mixing 2%, 5%, 10%, and 20% KSR in the gfCDM medium. On and after Day 18, the oxygen partial pressure during culture was set to 40%. The differentiation of the tissue was analyzed by a fluorescent antibody method.

Figure 2:
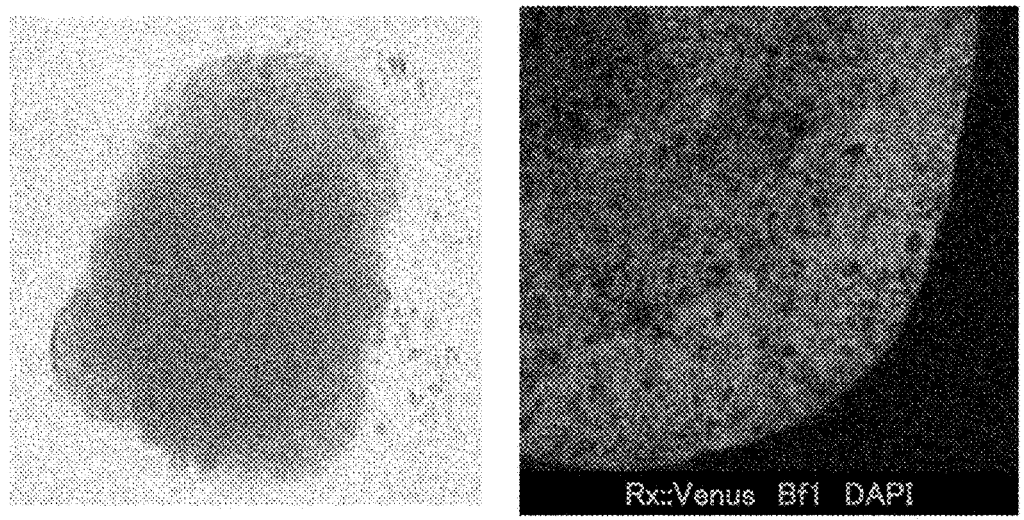
FIG. 2 shows differentiation using medium containing serum alternative KSR at a low concentration. Cell aggregates were formed (left), but differentiated into telencephalon (right). Rx: Venus: Green, Bf1: Red, DAPI: Blue.

An aggregate was formed on Day 3 of culture (left in FIG. 2), but, within the cell aggregate on Day 30 of culture, Rx was not expressed and broad expression of Bf1 was observed (right in FIG. 2). It was thought that the cells were differentiated into telencephalic precursor cells.

(3) Study 2 on Components in Medium (Use of Bone Morphogenetic Protein Signal Transduction Pathway Activating Substance)

Based on the thought that the positional shift to the telencephalon was caused by various growth factors included in KSR, the addition of a bone morphogenetic protein signal transduction pathway activating substance was decided. Specifically, differentiation induction was attempted under the following conditions. From Day 6 after the SFEBq method was performed, the cells were cultured in suspension in a medium containing about 3.0 nM bone morphogenetic protein signal transduction pathway activating substance. From the medium exchange on Day 15 of culture, the exchange of a half of the medium with a medium free from a bone morphogenetic protein signal transduction activating substance was decided (therefore, on and after Day 15 of culture, the concentration of the bone morphogenetic protein signal transduction activating substance is half that before medium exchange). The frequency of medium exchange is once every 3 days.

Figure 3:
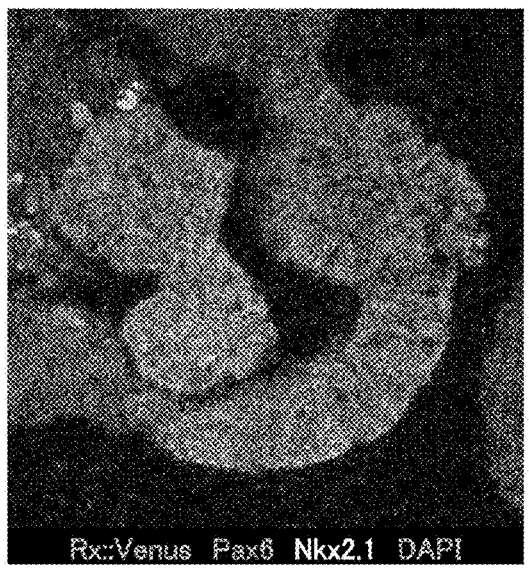
FIG. 3 shows differentiation using medium containing serum alternative KSR at a low concentration and containing BMP4 signal. The hypothalamic marker Rx and the dorsal marker Pax6 became co-positive, but the retinal marker Chx10 also became positive. Rx: Venus: Green, Pax6: Red, Nkx2.1 (NKX2-1 NK2 homeobox 1): White, DAPI: Blue, Chx 10: Red.
Figure 3:

By adding the BMP4 signal, Rx as a hypothalamic marker and Pax6 as a dorsal marker became co-positive on Day 30 of culture (left in FIG. 3). However, the retinal marker Chx10 also became positive (right in FIG. 3), revealing that a neural retina was generated.

(4) Study 3 on Components in Medium (Use of Substance Acting on the Shh Signaling Pathway)

Figure 4:
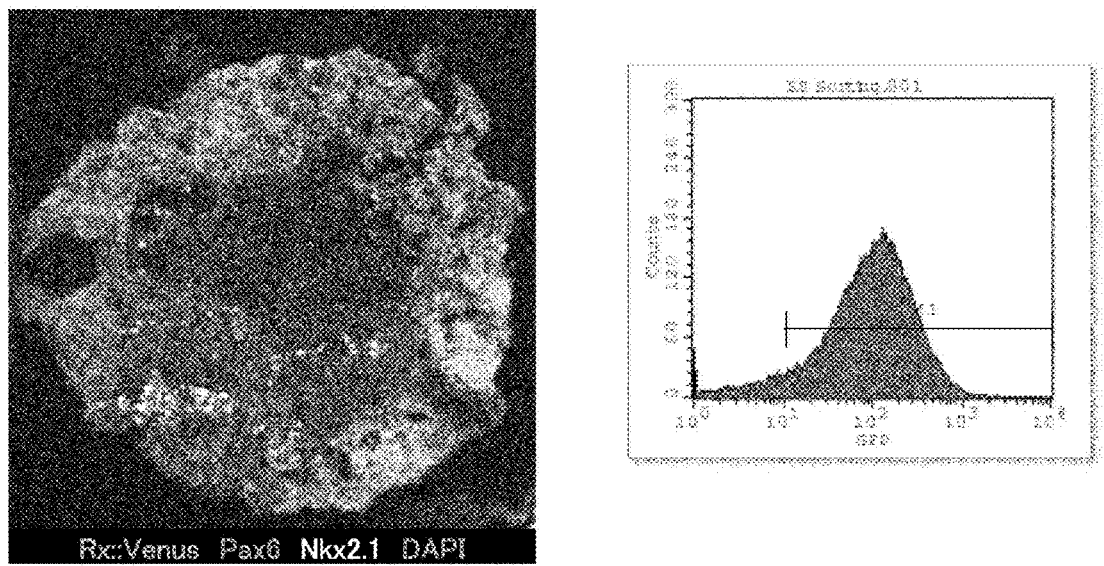
FIG. 4 shows differentiation using medium containing serum alternative KSR at a low concentration, containing BMP4 signal, and containing Shh signal (SAG which is a Shh agonist). It became possible to differentiate into hypothalamic precursor cells (left). Rx: Venus: Green, Pax6: Red, Nkx2.1: White, DAPI: Blue. The differentiation efficiency of hypothalamic precursor cells exceeded 80% (right).

Based on the thought that the induction of differentiation into the neural retina was caused by lack of ventralization factor, the addition of the Shh signal of the ventralization factor (SAG which is a Shh agonist) was decided. Specifically, differentiation induction was attempted under the following conditions. From Day 6 after the SFEBq method was performed, the cells were cultured in suspension in a medium containing a small amount of a bone morphogenetic protein signal transduction pathway activating substance (1.5 to 2.0 nM as a specific example) and a small amount of SAG (0.5 µM as a specific example). From Day 12, the concentration of the bone morphogenetic protein signal transduction pathway activating substance alone was gradually decreased, and the concentration of SAG was maintained. By adding the Shh signal, cell aggregates co-positive for Rx and Pax6 and Chx10 negative were observed on Day 30 of culture, and the differentiation into hypothalamic precursor cells became possible (left in FIG. 4). The differentiation efficiency of hypothalamic precursor cells exceeded 80% (right in FIG. 4).

(5) Selective Differentiation into Dorsal Hypothalamus or Ventral Hypothalamus

For separately producing dorsal hypothalamus and ventral hypothalamus, further study was made. The concentrations of the bone morphogenetic protein signal transduction pathway activating substance and SAG added and addition timings thereof and the presence or absence of the addition of an Akt inhibitor, concentration of the Akt inhibitor added and addition timing thereof were studied. As the dorsal hypothalamus conditions, the culture conditions in (4) were adopted. On the other hand, in order to promote the differentiation into ventral hypothalamus, the final concentration of BMP4 was changed to 1.0 nM. In addition, the Akt inhibitor was added at a final concentration of 0.5 µM from Day 6 of culture.

Under the dorsal hypothalamic conditions, most of Rx: Venus positive cells showed Pax6 positive (left in FIG. 5). It is considered that the cells were differentiated into precursor cells of the dorsal hypothalamus. On the other hand, under the ventral hypothalamic conditions, most of Rx: Venus positive cells showed Nkx2.1 positive (right in FIG. 5). It is considered that the cells were differentiated into precursor cells of ventral hypothalamus.

As described above, dorsal hypothalamus and ventral hypothalamus were successfully separately produced, i.e., the cells were successfully selectively differentiated into dorsal hypothalamus or ventral hypothalamus, by adjusting the concentration of KSR and the concentrations of the BMP4 signal and the Shh signal (SAG) and by adding or not adding a small amount of an Akt inhibitor which is another ventralization signal.

(6) Optimization of Dorsal Hypothalamic Induction Condition

Figure 6:
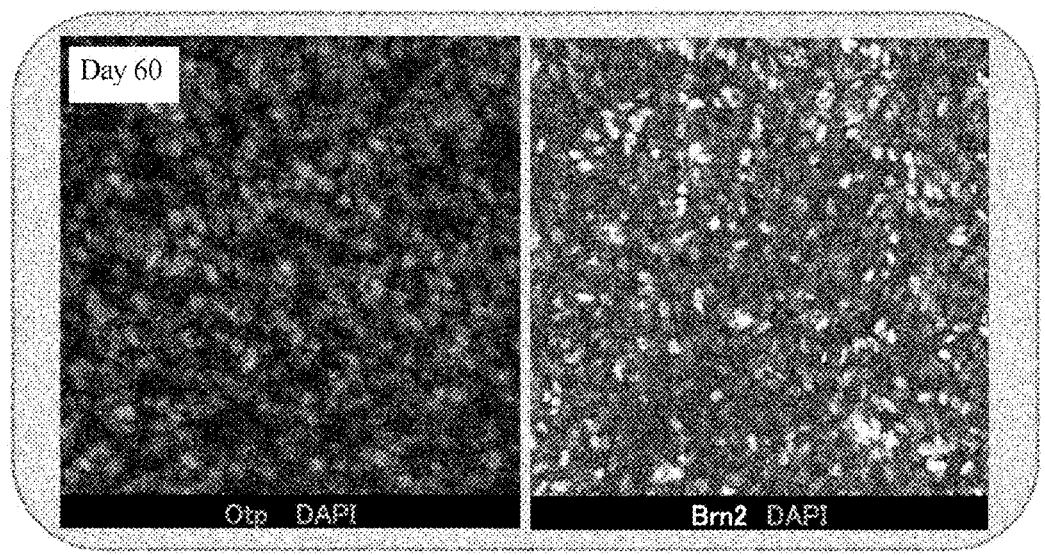
FIG. 6 shows a cell structure on Day 60 of culture under dorsal hypothalamic induction conditions. Opt: Red, DAPI: Blue, Brn2: White.
Figure 7:
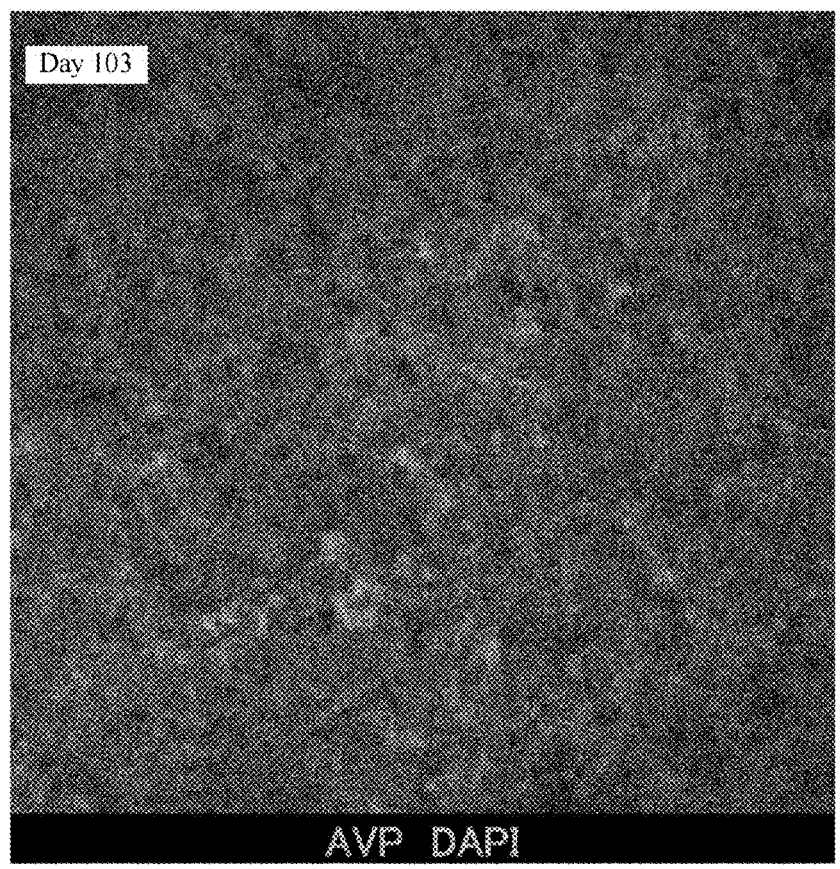
FIG. 7 shows a cell structure on Day 103 of culture under the dorsal hypothalamic induction conditions (without dissociation culture). AVP: Red, DAPI: Blue.

As a result of continuing suspension culture under the dorsal hypothalamus induction conditions, the expression of Otp and Brn2 (generally, Otp and Brn2 positive hypothalamus is thought to be in the precursor state of AVP neurons) was confirmed on Day 60 of culture (FIG. 6), and a small number of AVP-positive cells were observed on Day 103 of culture (FIG. 7). In order to improve the induction efficiency, the incorporation of dissociation culture, which is considered to be advantageous in neurogenesis, was decided. Specifically, differentiation induction was attempted under the following conditions. Cell aggregates were dispersed, and cells were seeded at $2\times10^4$ to $40\times10^4$ cells/cm$^2$ on glass plates coated with Laminin, Poly-D-Lysine and Matrigel, respectively, and subjected to plane culture in media obtained by adding NT3, BDNF, CNTF, and FBS, respectively, to a DFNB medium. Medium exchange was carried out at a frequency of once every 3 days.

Figure 8:
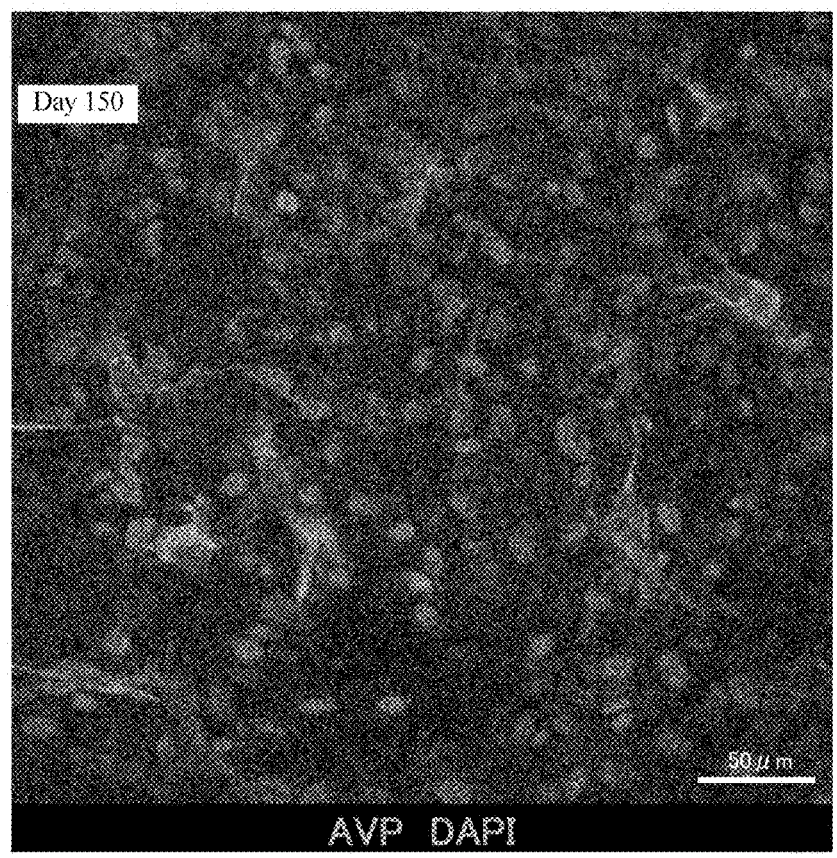
FIG. 8 shows a cell structure on Day 150 of culture under the dorsal hypothalamic induction conditions (with dissociation culture). AVP: Red, DAPI: Blue.
Figure 9:
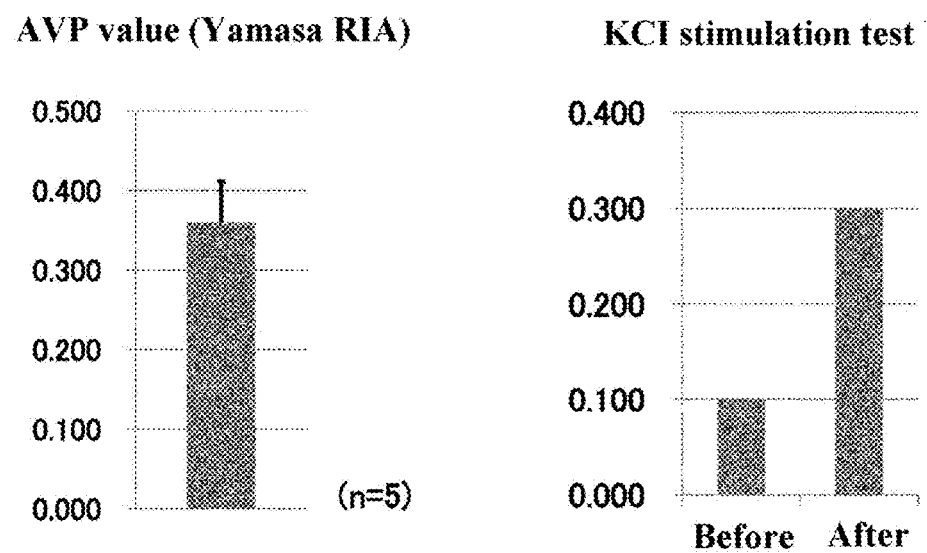
FIG. 9 shows measurement results (left) of AVP hormone produced by a cellular structure constructed under the dorsal hypothalamic induction conditions (with dissociation culture) (left) and results (right) of KCl stimulation test.

As a result of differentiation induction under the above conditions, the appearance of AVP neurons was confirmed on Day 150 of culture (FIG. 8). In order to verify the maturity and function of the AVP neurons, AVP hormone measurement and stimulation test were performed by the following procedures using the cells on Day 180 of culture as a sample. First, the medium after used for cell culture for 3 days was recovered, and the AVP hormone in the medium was measured by RIA method. As a result of the measurement, it was confirmed that the induced AVP neurons actually secreted AVP hormone (left in FIG. 9). In addition, they responded well to stimulation with potassium chloride (cultured with an isotonic solution containing 0.1% potassium chloride for 30 minutes) (right in FIG. 9).

(7) Appearance of Other Hypothalamic Neurons

Differentiation induction was performed under the above conditions (column (6)), and OXT neurons, TRH neurons, CRH neurons, NPY neurons, AgRP neurons, POMC neurons, MCH neurons, and Orexin neurons were detected by the following method on Day 150 of culture.

Figure 10:
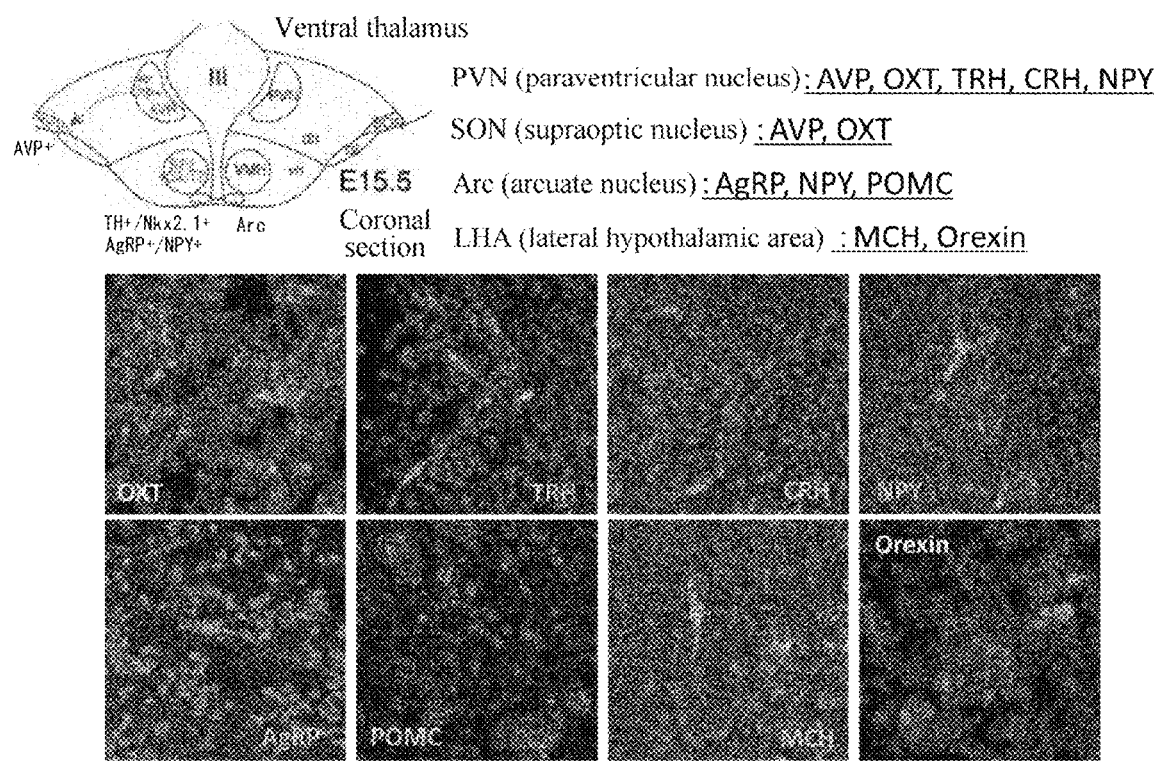
FIG. 10 shows hypothalamic neurons (lower) observed in the cellular structures on Days 130 to 150 under the dorsal hypothalamic induction conditions (with dissociation culture) and the localization (upper) of each hypothalamic neuron in a living body. OXT: Green, TRH: Red, CRH: Red, NPY: Red, AgRP: Red, POMC: Red, MCH: Red, Orexin: Green.
Figure 11:
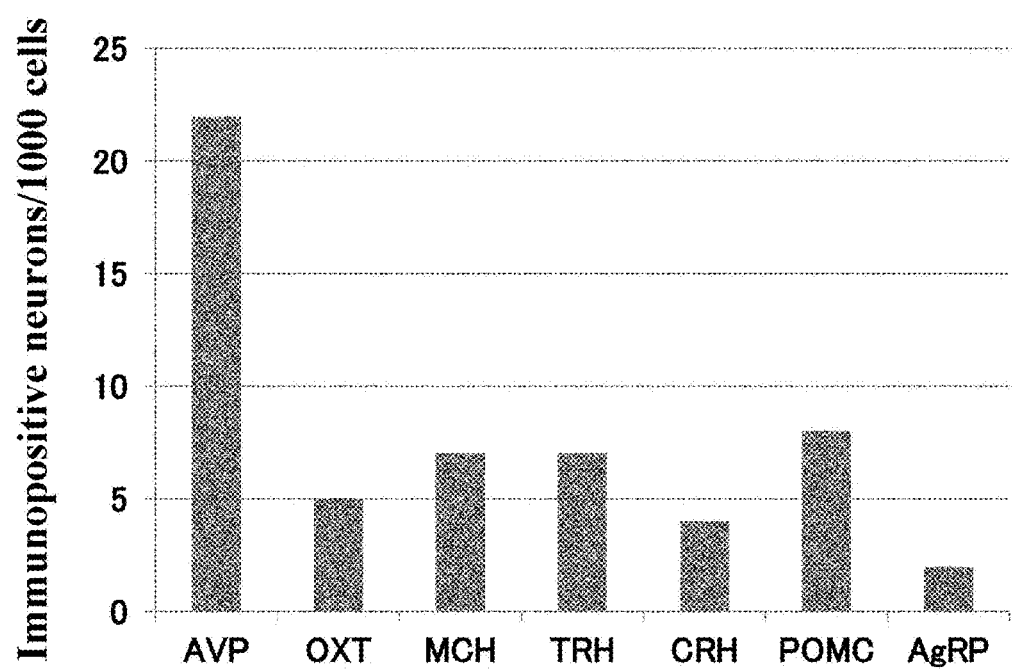
FIG. 11 shows comparison of differentiation efficiencies of the respective hypothalamic neurons. Comparison was made in terms of the numbers of immunostaining positive neurons per 1000 nerve cells.

Immunostaining was performed on Day 150 of culture, and it was confirmed that hypothalamic neurons (OXT neurons, TRH neurons, CRH neurons, NPY neurons, AgRP neurons, POMC neurons, MCH neurons, and Orexin neurons) other than AVP neurons appeared (FIG. 10). From the detection results, the differentiation efficiencies of the respective hypothalamic neurons were compared (FIG. 11). AVP neurons were induced efficiently.

Figure 12:
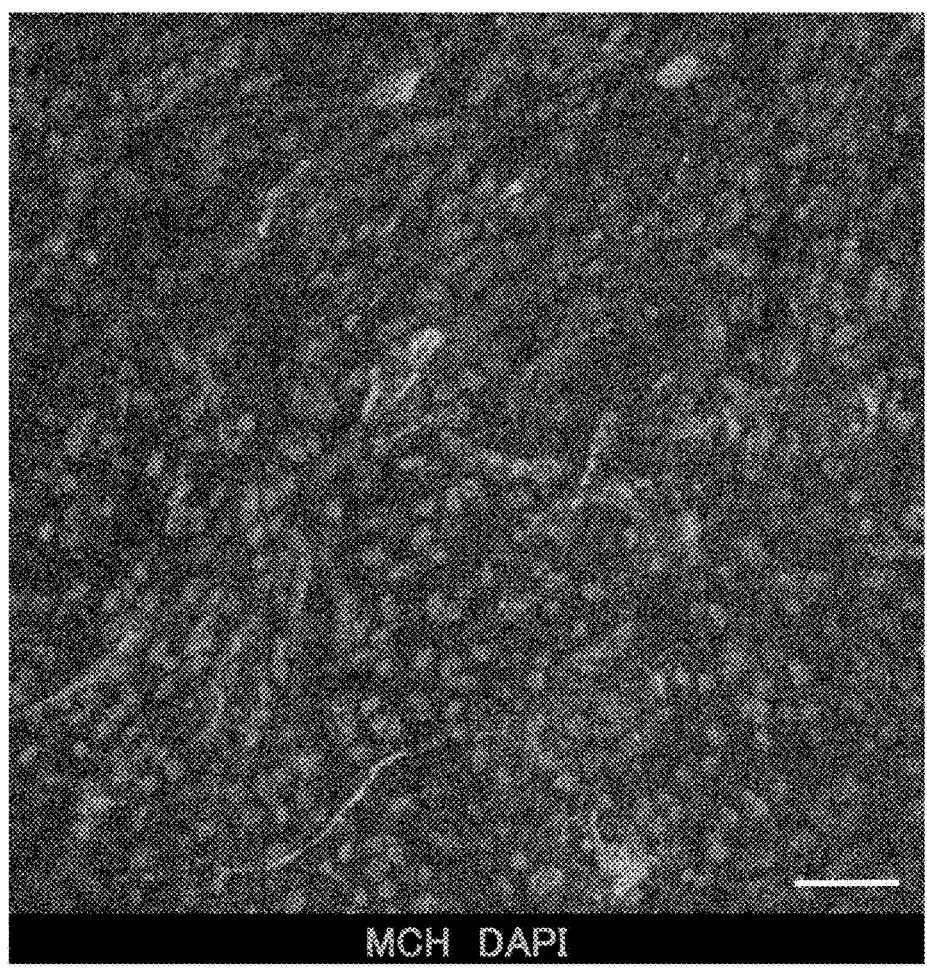
FIG. 12 shows a cell structure on Day 150 of culture under the ventral hypothalamic induction conditions. MCH: Red, DAPI: Blue.
Figure 15:
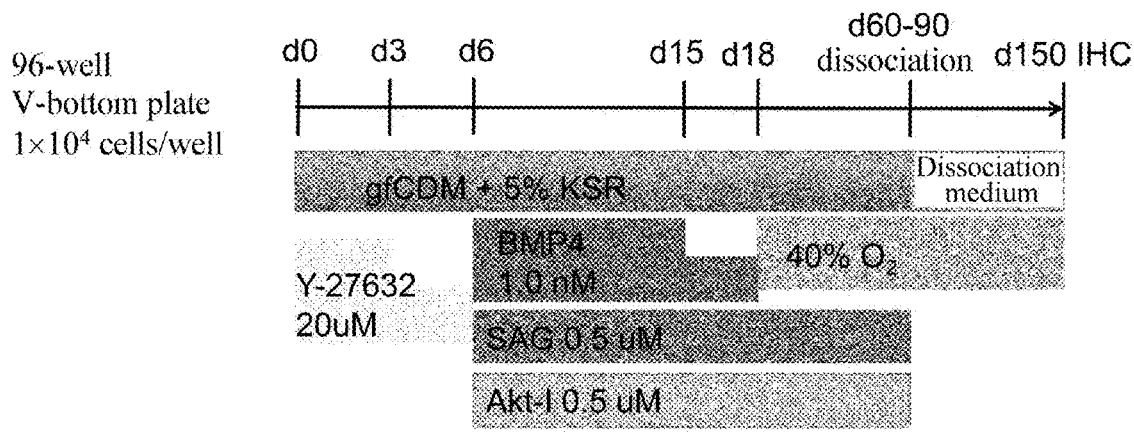
FIG. 15 is a schematic diagram of a ventral hypothalamus inducing method.

On the other hand, when the cells were cultured under the ventral hypothalamus induction conditions (FIG. 15), ventral hypothalamic neurons such as MCH neurons were observed at a higher rate than that under the dorsal hypothalamic induction conditions (FIG. 12).

2. Simultaneous Maturation of Hypothalamus and Pituitary

Figure 17:
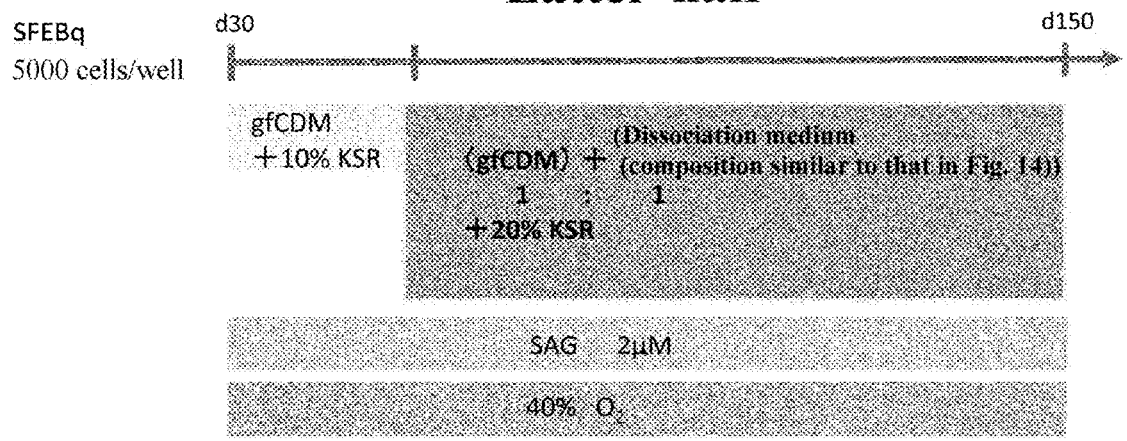
FIG. 17 is a schematic diagram of the simultaneous maturation method of hypothalamus and pituitary (latter half).

Since hypothalamus and pituitary are originally functionally inseparable, a structure in which hypothalamus and pituitary are functionally integrated is extremely useful as a tool, for example, for drug screening or as an implant material. Therefore, the following study was made for constructing a structure in which hypothalamus and pituitary were functionally integrated. Ozone C et al. reported a method for inducing differentiation from human ES cells into pituitary (Functional anterior pituitary generated in self-organizing culture of human embryonic stem cells. Ozone C, Suga H, Eiraku M, Kadoshima T, Yonemura S, Takata N, Oiso Y, Tsuji T, Sasai Y. Nat Commun. 2016 Jan. 14; 7: 10351. Doi: 10.1038/ncomms 10351.). When this method was reproduced, early hypothalamic precursor cells and pituitary primordium were simultaneous induced, as reported. However, the differentiation into hypothalamic tissue stops in the middle of culture and does not reach neurons expressing a hypothalamic hormone. Therefore, in the first half of culture, there were adopted conditions in accordance with the dorsal hypothalamic induction conditions (provided that the concentrations of the bone morphogenetic protein signal transduction pathway activating substance and the substance acting on the Shh signaling pathway were set high. Also, from medium exchange on Day 18 of culture, a half of the medium was exchanged with a medium free from a bone morphogenetic protein signal transduction activating substance). In the latter half of culture, the composition of the medium to be used was improved to make it suitable for differentiation into not only pituitary but also hypothalamus. Specifically, a medium obtained by mixing the medium used in the above step (ii) and the medium used in the dissociation culture in a volume ratio of 1:1 and adding 20% of a serum alternative (for example, KSR) was used (see FIG. 17) to continue suspension culture.

Figure 13:
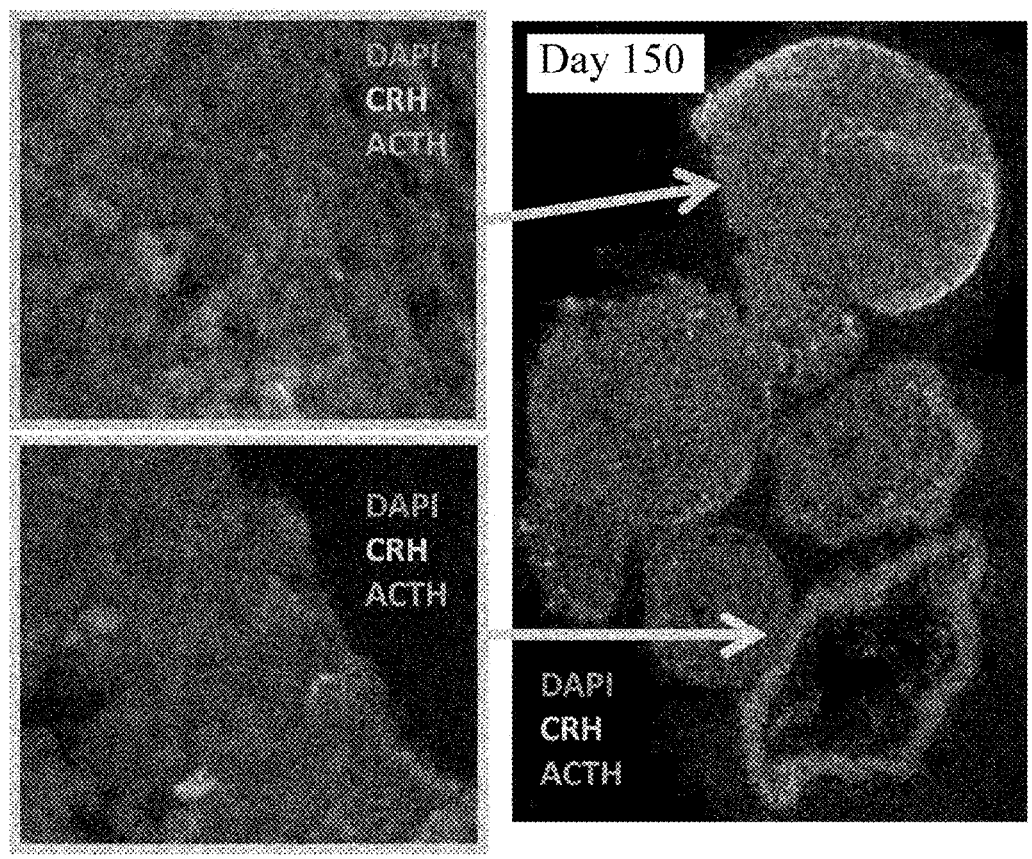
FIG. 13 shows cell structure on Day 150 of culture under simultaneous maturation conditions of hypothalamus and pituitary. DAPI: Blue, CRH: Green, ACTH: Red.

Analysis by the fluorescent antibody method on Day 150 of culture revealed that CRH neurons exist in the hypothalamic tissue and that ACTH neurons exist in pituitary tissue (FIG. 13). That is, differentiation into/maturation of both hypothalamus and pituitary from one cell mass were successful.

3. Conclusion

Figure 14:
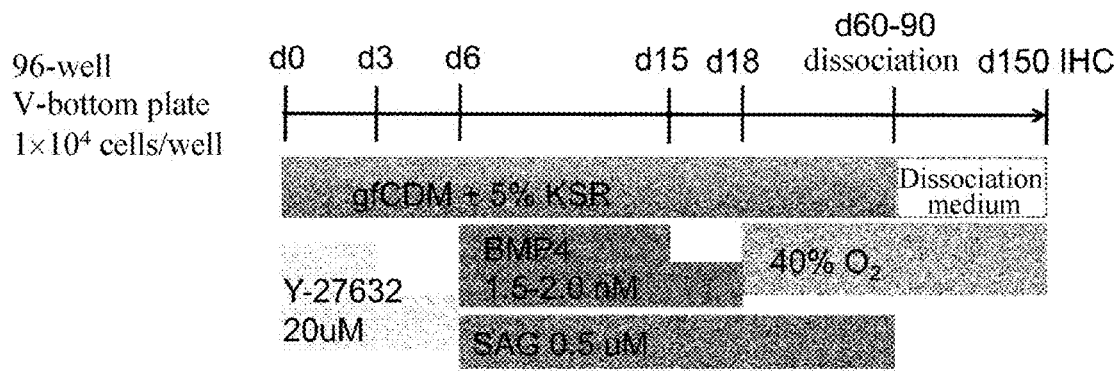
FIG. 14 is a schematic diagram of a dorsal hypothalamus inducing method.
Figure 16:
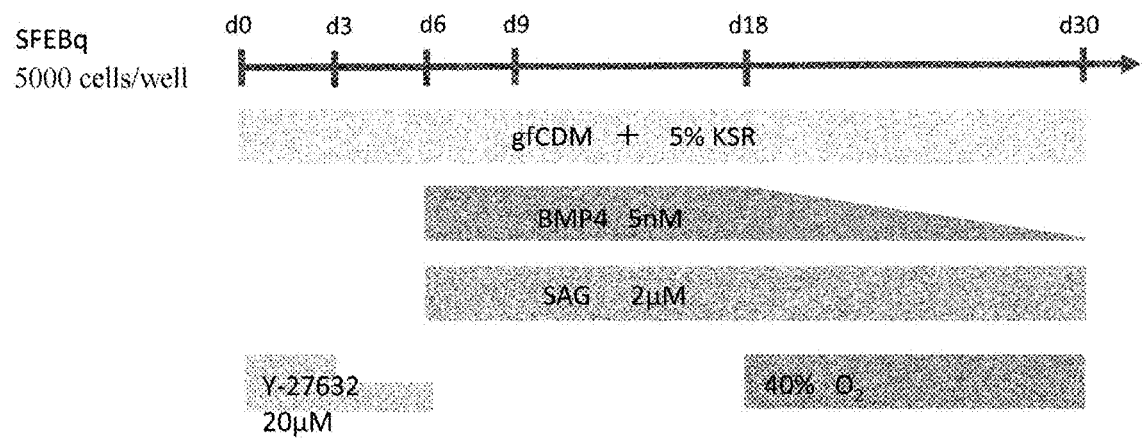
FIG. 16 is a schematic diagram of simultaneous maturation method of hypothalamus and pituitary (first half).

Based on the above studies, the conditions for inducing differentiation into the dorsal hypothalamus and inducing differentiation into ventral hypothalamus have been found. In addition, the differentiation inducing conditions that enable construction of a structure in which hypothalamus and pituitary are functionally integrated have also been found by simultaneous maturation of hypothalamus and pituitary. Specific examples (outline) of suitable differentiation inducing conditions are shown in FIG. 14 (dorsal hypothalamus), FIG. 15 (ventral hypothalamus), and FIGS. 16 and 17 (simultaneous maturation of hypothalamus and pituitary).

Figure 25:
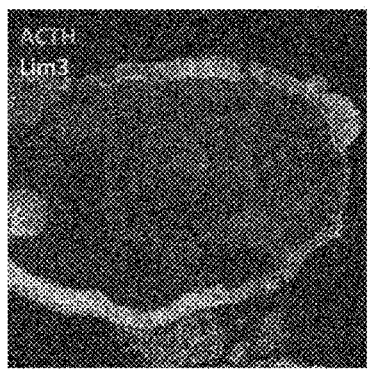
FIG. 25 shows immunostaining images (left and center) of structure obtained by differentiation induction by a previously reported method and a corresponding schematic diagram (right). ACTH: Red, Lim 3: Green, Rx: Green, AVP: Red.
Figure 25:
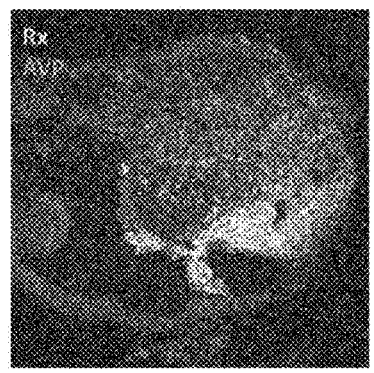
Figure 25:
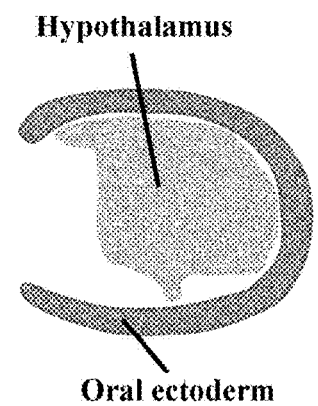

It was reported that differentiation of human ES cells into the anterior pituitary was successful (Ozone C et al., Functional anterior pituitary generated in self-organizing culture of human embryonic stem cells. Nat Commun. 2016 Jan. 14; 7: 10351.). However, when the characteristics of the cell aggregate obtained by differentiation induction under the conditions indicated therein were evaluated by the fluorescent antibody method, no hypothalamic neuron (AVP neuron or the like) was detected (FIG. 25), and no finally differentiated functional neuron appeared. Therefore, the new differentiation inducing conditions found by the above studies are distinct from those indicated in the report in that a structure including functional hypothalamic neurons can be constructed.

B. Differentiation Induction from Human iPS Cells

In order to confirm that the differentiation inducing conditions found by the above studies induce hypothalamus from human iPS cells and is effective for simultaneous maturation of hypothalamus and pituitary, the following verification experiment was conducted.

1. Appearance of Hypothalamic AVP Neuron

Figure 18:
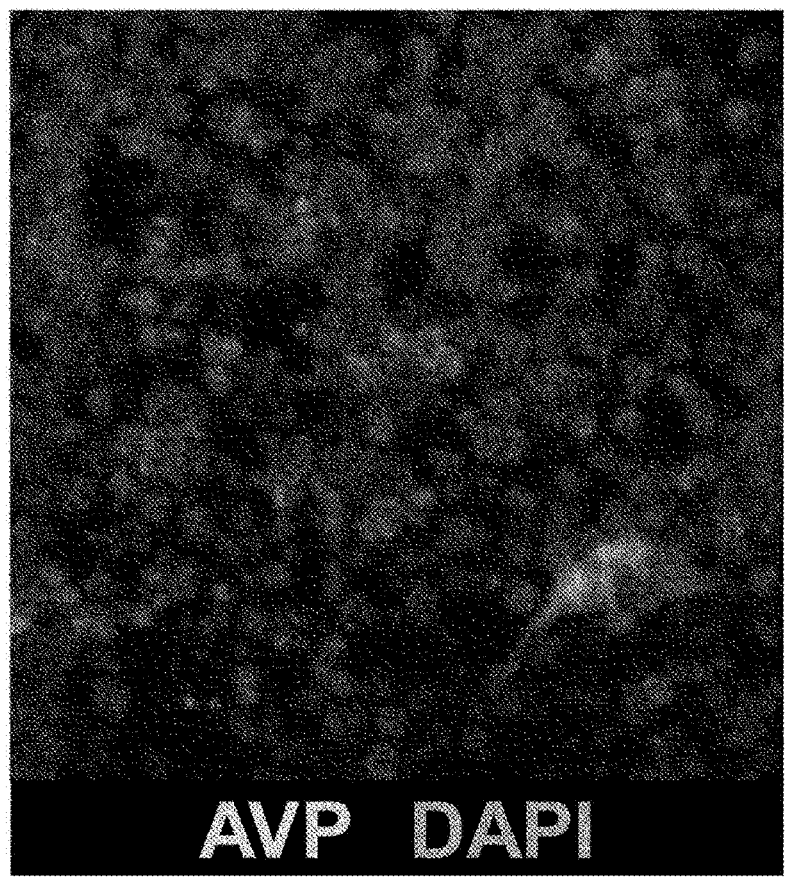
FIG. 18 shows an immunostaining image of hypothalamic AVP neurons obtained by differentiating human iPS cells (201B7 strain). AVP: Green, DAPI: Blue.

Human iPS cells (201B7 strain) were cultured under the dorsal hypothalamic induction conditions (see column A.1. (6)) found by the study using human ES cells. As a result, the appearance of AVP neurons was confirmed (FIG. 18).

Figure 19:
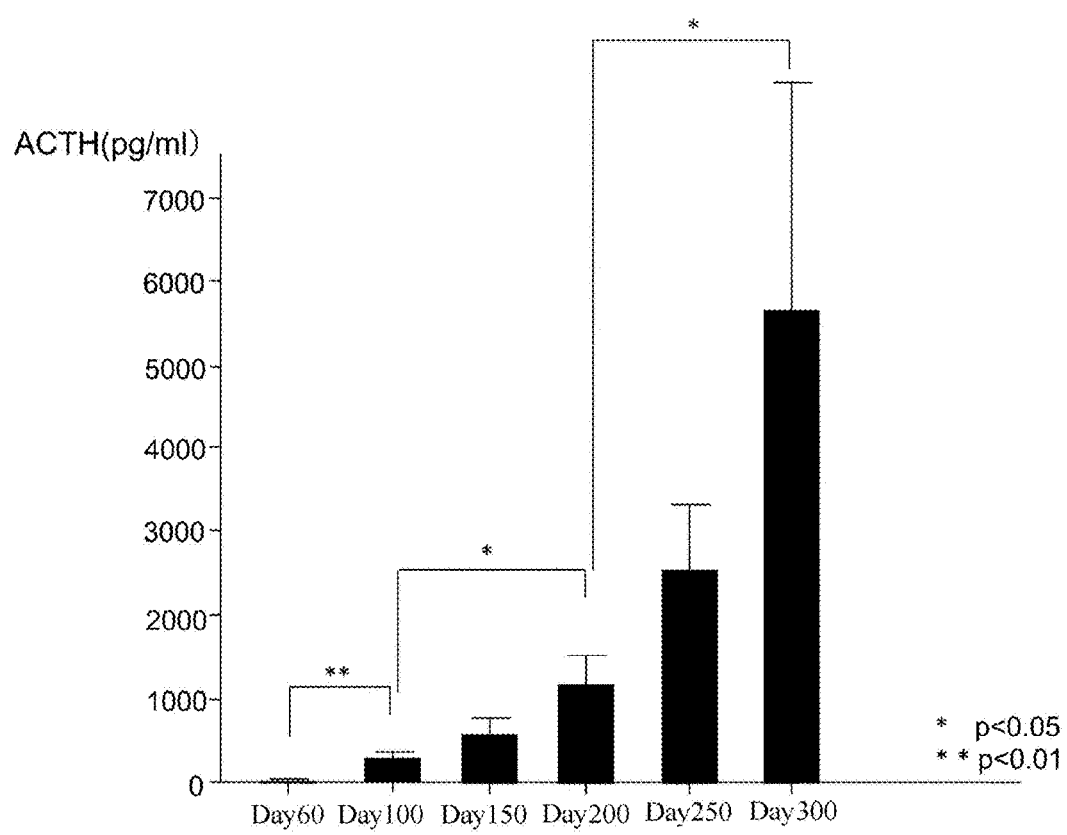
FIG. 19 shows ACTH secretion ability of a structure obtained by culturing human iPS cells under simultaneous maturation conditions of hypothalamus and pituitary. * $p<0.05$, ** $p<0.01$

2. Simultaneous Maturation of Hypothalamus and Pituitary (1) Maturation of Pituitary Human iPS cells (201B7 strain) were cultured under conditions (see column A.2) that were effective for simultaneous maturation of hypothalamus and pituitary. Pituitary tissue and hypothalamic tissue were observed on Day 60 of culture, and ACTH neurons were detected in pituitary tissue. In addition, the amount of ACTH secreted from pituitary tissue was increased by long-term culture (FIG. 19), and it was confirmed that the maturation of pituitary tissue had progressed with the lapse of culture time.

(2) Effect Obtained by Adjacency of Hypothalamus and Pituitary

Figure 20:
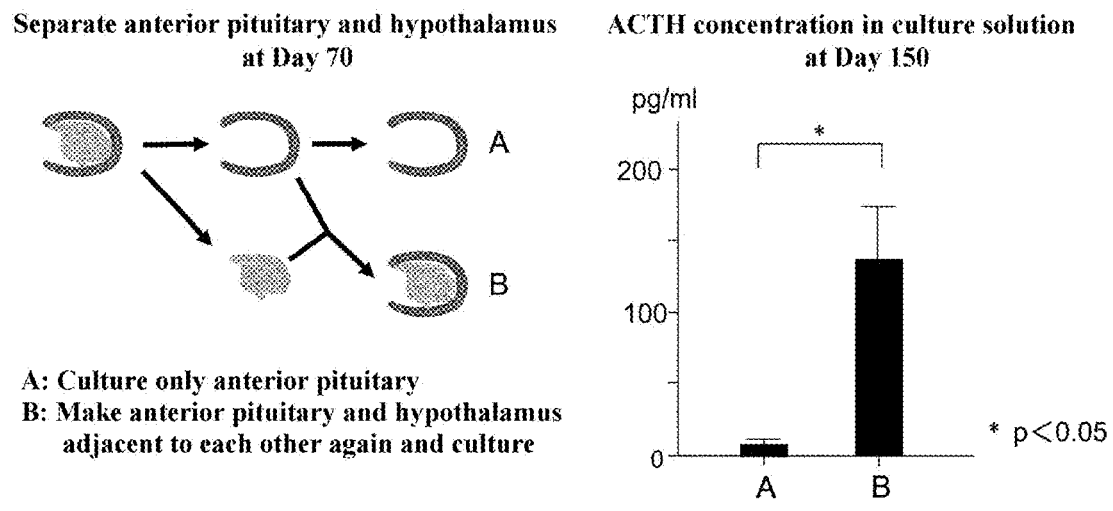
FIG. 20 shows comparison in ACTH secretion ability between case (A) where pituitary (anterior lobe) and hypothalamus were separated from each other and only pituitary (anterior lobe) was cultured, and (B) case where pituitary (anterior lobe) and hypothalamus were made re-adjacent to each other and cultured. The concentration of ACTH in the culture solution on Day 150 of culture was measured (right). * $p<0.05$

Between when the pituitary tissue and the hypothalamic tissue were separated on Day 70 of culture and culture was continued with the pituitary tissue alone (FIG. 20A) and when the pituitary tissue and the hypothalamic tissue were made adjacent again and cultured (FIG. 20B), the maturation of tissues was compared and evaluated. When the ACTH concentration in the medium was measured on Day 150 of culture, the ACTH concentration was significantly high when the pituitary tissue and the hypothalamic tissue were made adjacent to each other again and cultured (right in FIG. 20). This result suggests that culturing the two tissues adjacent to each other is extremely important for the maturation thereof.

(3) Evaluation 1 of Function of Pituitary Tissue

Figure 21:
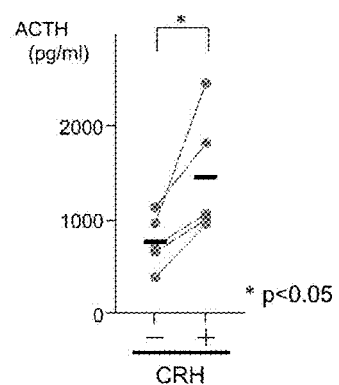
FIG. 21 is a schematic diagram (right) showing the outline of ACTH stimulation test by CRH and test results (left). * $p<0.05$. Immunostaining image in the center. DAPI: Blue, ACTH: Green, CRH-R1: Red.
Figure 21:
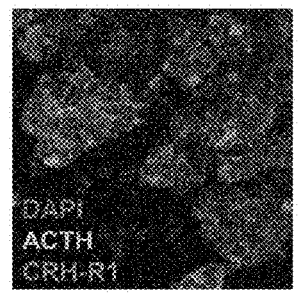
Figure 21:
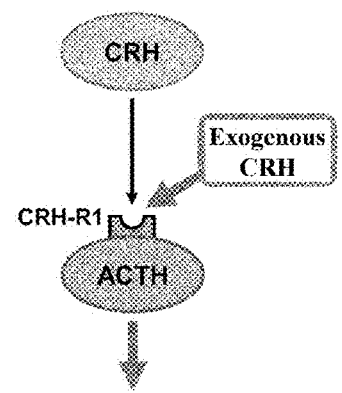

In order to evaluate the function of pituitary tissue obtained by culture under the conditions in (1), an ACTH stimulation test using CRH (right in FIG. 21) was performed. The test method was in accordance with the previously reported method (Ozone C et al., Functional anterior pituitary generated in self-organizing culture of human embryonic stem cells. Nat Commun. 2016 Jan. 14; 7: 10351.) (CRH was added at 5 μg/ml). As a result of the test, it was shown that ACTH was secreted in response to CRH, that is, functional ACTH neurons were obtained (left side in FIG. 21). In addition, it was confirmed, by analysis by the fluorescent antibody method, that ACTH positive cells were CRH-R1 positive (center in FIG. 21).

(4) Evaluation 2 of Function of Pituitary Tissue

Figure 22:
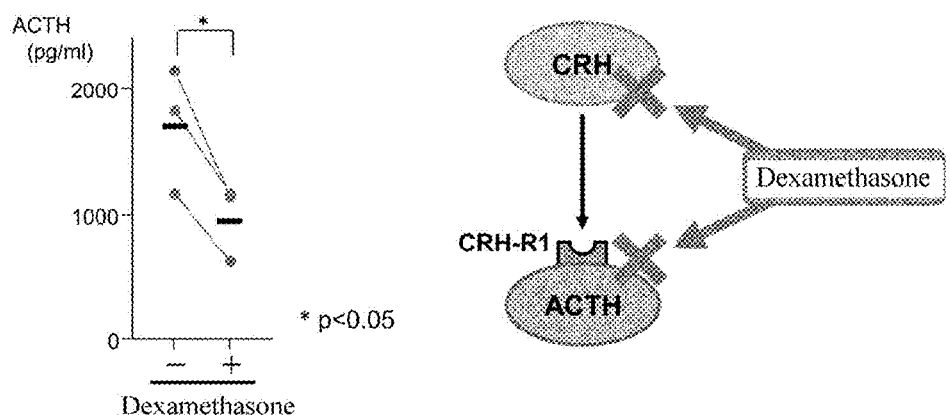
FIG. 22 is a schematic drawing (right) showing the outline of ACTH suppression test by dexamethasone and test results (left). * p<0.05

In order to further evaluate the function of pituitary tissue obtained by culture under the conditions in (1), an ACTH suppression test using dexamethasone (right in FIG. 22) was performed. At the time of stimulation with CRH addition, dexamethasone was added at 500 ng/ml (test group), and the amount of ACTH secreted was compared with that when no dexamethasone was added (control group). As a result of the test, the secretion of ACTH was suppressed by dexamethasone (left in FIG. 22). That is, it was confirmed that a functional pituitary tissue in which negative feedback occurred by the steroid was formed.

(5) Evaluation 3 of Function of Pituitary Tissue

Figure 23:
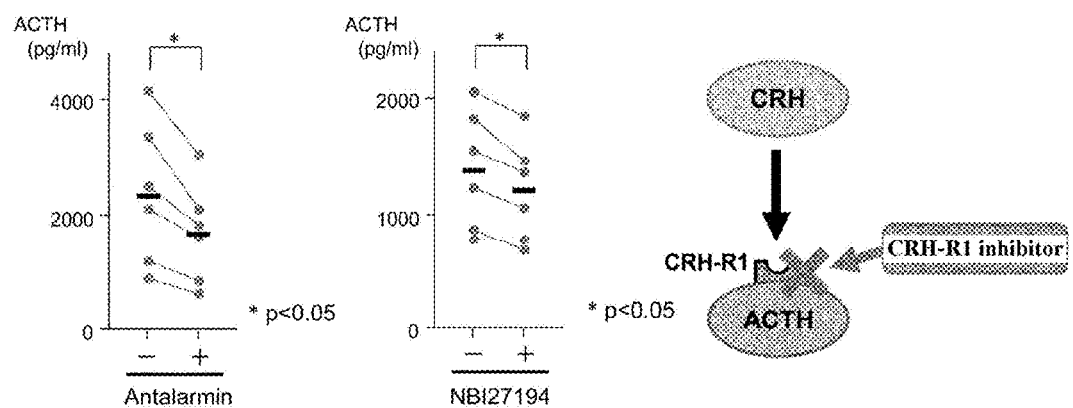
FIG. 23 is a schematic drawing (right) showing the outline of ACTH suppression test by CRH-R1 inhibitor and test results (left and center). * p<0.05

To further evaluate the function of pituitary tissue obtained by culture under the conditions in (1), an ACTH suppression test using a CRH-R1 inhibitor (Antalarmin, NBI2719) was performed (right in FIG. 23). A CRH-R1 inhibitor was added at a dose of $10^{-5}$ M (test group) at the time of stimulation with CRH addition, and the amount of ACTH secreted was compared with that when no CRH-R1 inhibitor was added (control group). As a result of the test, the secretion of ACTH was suppressed by the CRH-R1 inhibitor (left and center in FIG. 23). This result suggests that ACTH neurons (ACTH positive cells) function under the control of CRH neurons (CRH positive cells).

Figure 24:
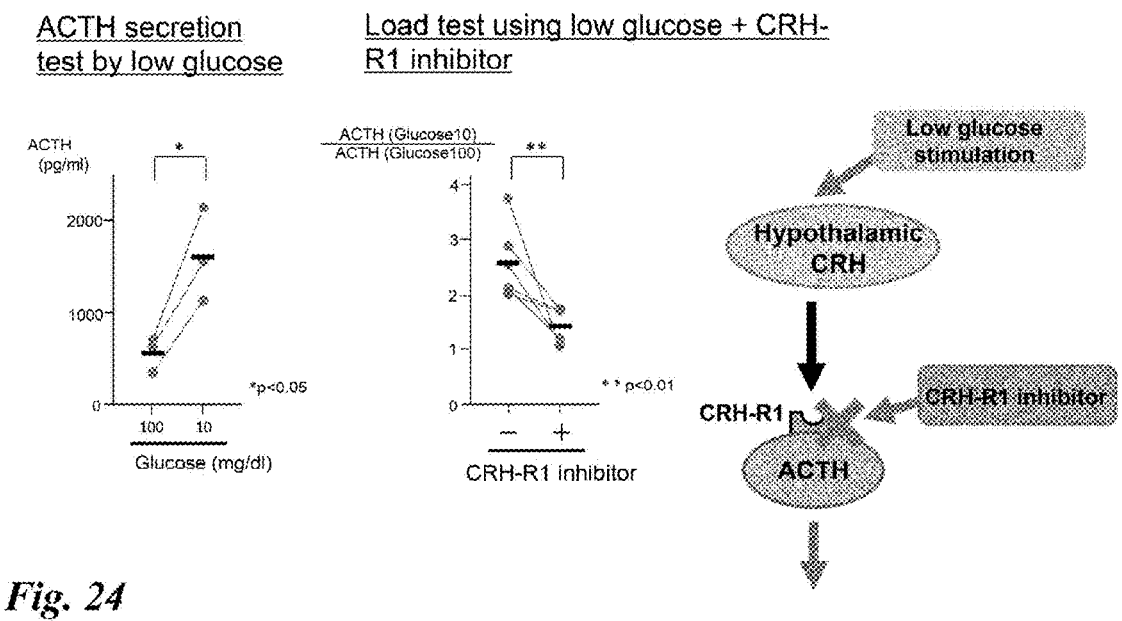
FIG. 24 is a schematic diagram (right) showing the outline of ACTH secretion test with low glucose and low glucose +CRH-R1 inhibitor load test and test results (left and center). * p<0.05, ** p<0.01

(6) Evaluation of Function of Structure in which Hypothalamus and Pituitary are Integrated The reactivity of the structure obtained by simultaneous maturation to hypoglycemic stress was evaluated (right in FIG. 24). As a result of examining the change in the amount of ACTH secreted by low glucose stimulation, the amount of ACTH secreted increased in response to low glucose stimulation (left in FIG. 24), and this reactivity was attenuated by the CHRH-R1 inhibitor (center in FIG. 24). These results suggest that ACTH neurons (ACTH positive cells) contained in the structure obtained by simultaneous maturation function under the control of hypothalamus, and demonstrate that a structure in which hypothalamus and pituitary are functionally integrated is formed.

INDUSTRIAL APPLICABILITY

According to the present invention, hypothalamic tissue can be efficiently induced from human pluripotent stem cells. The cellular structure constructed by the method of the present invention is useful, for example, as a tool for drug screening targeting hypothalamic disorders. It is also expected to be used as a therapeutic means (implant material) for hypothalamic disorders. On the other hand, the present invention also makes it possible to construct in vitro a cellular structure in which hypothalamic tissue and pituitary tissue are functionally integrated. The cellular structure is an extremely useful tool, for example, for drug screening targeting hypothalamus and/or pituitary, and can also be applied as an implant material.

The present invention is not limited to the description of the embodiments and examples of the present invention at all. Various modifications that can be easily achieved by those skilled in the art without departing from the claims also fall within the scope of the invention. The contents of the articles, the patent laid-open publications, patent publications, and the like specified herein shall be cited by incorporation in their entity.

The invention claimed is:

1. A method for producing a cellular structure comprising dorsal hypothalamic tissue, the method comprising the steps of:
   (1) culturing an aggregate of human pluripotent stem cells in suspension in a medium containing a bone morphogenetic protein signal transduction pathway activating substance and a substance acting on the Shh signaling pathway for 10 to 26 days,
   (2) further culturing the cell aggregate obtained in the step (1) in a medium containing a substance acting on the Shh signaling pathway, but not containing a bone morphogenetic protein signal transduction pathway activating substance for 20 to 100 days, and
   (3) dissociating the cell aggregate obtained in the step (2) into single cells and subjecting the dissociated single cells to dissociation culture for 40 to 110 days, in a medium comprising a ciliary neurotrophic factor (CNTF), a brain-derived neurotrophic factor (BDNF) or LM22A-4, a neurotrophin 3 (NT-3), a fetal bovine serum or a serum alternative, an N2 supplement, and a B27 supplement, and thereby obtaining a dorsal hypothalamic tissue comprising one or more neurons selected from the group consisting of vasopressin neurons secreting vasopressin, oxytocin neurons secreting oxytocin, thyrotropin releasing hormone neurons secreting thyrotropin releasing hormone, corticotropin releasing hormone neurons secreting corticotropin releasing hormone and neuropeptide Y neurons secreting neuropeptide Y; wherein the dissociation culture is performed under an oxygen partial pressure about between 35-60%;
   wherein the bone morphogenetic protein signal transduction pathway activating substance in the step (1) is BMP4, and the concentration thereof in the medium is 0.1 nM to 2.0 nM,
   wherein the substance acting on the Shh signaling pathway in the steps (1) and (2) is SAG, and the concentration thereof in the medium is 0.1 µM to 1.0 µM.

2. The producing method according to claim 1, wherein the step (2) is carried out under a high oxygen partial pressure condition.

3. The producing method according to claim 1, wherein the dorsal hypothalamic tissue comprises corticotropin releasing hormone neurons secreting corticotropin releasing hormone.

4. The producing method according to claim 1, wherein the suspension culture of step (1) and step (2) are carried out in the absence of feeder cells.

5. The producing method according to claim 1, wherein the aggregate in the step (1) is formed by culturing dispersed human pluripotent stem cells in suspension.

6. The producing method according to claim 5, wherein the suspension culture is carried out by SFEBq (Serum-free Floating culture of Embryoid Body-like aggregates with quick reaggregation) method.

7. The producing method according to claim 1,
   wherein the dorsal hypothalamic tissue contains a cell that is Rx positive, Pax6 positive, Nkx2.1 negative and Chx10 negative.

* * * * *